US012268219B2

(12) United States Patent
Fremaux et al.

(10) Patent No.: US 12,268,219 B2
(45) Date of Patent: Apr. 8, 2025

(54) LACTIC ACID BACTERIUM WITH A REDUCTION OF SENSITIVITY TO COS-TYPE BACTERIOPHAGES

(71) Applicant: DUPONT NUTRITION BIOSCIENCES APS, Copenhagen K (DK)

(72) Inventors: Christophe Fremaux, Dangé-Saint-Romain (FR); Philippe Horvath, Dangé-Saint-Romain (FR); Armelle Cochu-Blachère, Dangé-Saint-Romain (FR); Dennis Romero, New Century, KS (US); Sylvain Moineau, Québec (CA); Simon Labrie, Québec (CA)

(73) Assignee: International N&H Denmark ApS, Kongens Lyngby (DK)

( * ) Notice: Subject to any disclaimer, the term of this patent is extended or adjusted under 35 U.S.C. 154(b) by 610 days.

(21) Appl. No.: 17/429,555

(22) PCT Filed: Feb. 13, 2020

(86) PCT No.: PCT/EP2020/053676
§ 371 (c)(1),
(2) Date: Aug. 9, 2021

(87) PCT Pub. No.: WO2020/165301
PCT Pub. Date: Aug. 20, 2020

(65) Prior Publication Data
US 2022/0117247 A1    Apr. 21, 2022

Related U.S. Application Data

(60) Provisional application No. 62/805,388, filed on Feb. 14, 2019, provisional application No. 62/904,787, filed on Sep. 24, 2019.

(51) Int. Cl.
A23C 9/123     (2006.01)
A23K 10/18    (2016.01)
C12N 9/48      (2006.01)

(52) U.S. Cl.
CPC ........... *A23C 9/1238* (2013.01); *A23K 10/18* (2016.05); *C12N 9/485* (2013.01); *A23V 2400/237* (2023.08); *A23V 2400/249* (2023.08); *C12Y 304/11018* (2013.01)

(58) Field of Classification Search
CPC .... A23C 9/1238; A23C 9/1234; A23K 10/18; C12N 9/485; A23V 2400/237; A23V 2400/249; C12Y 304/11018; A23L 33/135
See application file for complete search history.

(56) References Cited

U.S. PATENT DOCUMENTS 4,683,202 A    7/1987  Mullis

FOREIGN PATENT DOCUMENTS

WO    01/70990 A1    9/2001
WO    2018/197495 A1    11/2018

OTHER PUBLICATIONS

Guedon et al. (J Bacteriol, 2001, 183(12):3614-3622) (Year: 2001).*
GenPept Database Accession No. AE006294_5 (Jan. 30, 2014, 2 pages) (Year: 2014).*
Deveau et al. (J Bacteriol, 2008, 190:1390) (Year: 2008).*
Timmerman et al. (Int J Food Microbiol, 2004, 96:219) (Year: 2004).*
GenPept Accession No. AKB98164.1 (May 27, 2015, 2 pages) (Year: 2015).*
NCBI Accession No. EHE91936.1 (Oct. 29, 2011, 2 pages) (Year: 2011).*
Lawyer et al. (Genome Res, 1997, 2:275) (Year: 1997).*
UniProt Accession No. A0A3D0CME9 (Jan. 16, 2019, 2 pages) (Year: 2019).*
Singh et al. (Curr. Protein Pept. Sci. 18:1-11, 2017) (Year: 2017).*
UniProt Accession No. V8LSK4 (Feb. 19, 2014, 2 pages) (Year: 2014).*
Zhang et al. (Structure 26:1474-1485, 2018) (Year: 2018).*
UniProt Accession No. A0A1H9QQK0_9STRE (Dec. 5, 2018, 2 pages) (Year: 2018).*
Li et al. (Biochem, 2004, 43:7892) (Year: 2004).*
Arya et al., Discovery of a New Genetic Variant of Methionine Aminopeptidase from *Streptococci* with Possible Post-Translational Modifications: Biochemical and Structural Characterization, PLOS One, vol. 8, Issue 10, e75207, Oct. 2013, 1-7.
De Groot, UNIPROT, Methionine aminopeptidase, XP002791964, Database Accession No. A0A1H9QQKO, Apr. 12, 2017, 2 pp.
De Groot, UNIPROT, Methionine aminopeptidase, XP002798692, Database Accession No. A0A1H9QQKO, Apr. 12, 2017, 1 p.
Duplessis et al., Characterization of *Streptococcus thermophilus* Host Range Phage Mutants, Applied and Environmental Microbiology, vol. 72, No. 4, Apr. 2006, 3036-3041.
Labrie et al., A mutation in the methionine aminopeptidase gene provides phase resistance in *Streptococcus thermophilus*, Scientific Reports, vol. 9, No. 1, Sep. 25, 2019, 1-11.
Lucchini et al., Broad-Range Bacteriophage Resistance in *Streptococcus thermophilus* by Insertional Mutagenesis, Virology, 275, Sep. 2000, 265-277.
Matthes et al., Simultaneous rapid chemical synthesis of over one hundred oligonucleotides on a microscale, The Embo Journal, vol. 3, No. 4, Apr. 1984, 801-805.
Mcdonnell et al., Generation of Bacteriophage-Insensitive Mutants of *Streptococcus thermophilus* via an Antisense RNA CRISPR-Cas Silencing Approach, Applied and Environmental Microbiology, vol. 84, Issue 4, Feb. 2018, 1-14.
Saiki et al., Primer-Directed Enzymatic Amplification of DNA with a Thermostable DNA Polymerase, Science 239, Jan. 1988, 487-491.

(Continued)

*Primary Examiner* — David Steadman
*Assistant Examiner* — Joseph R Spangler

(57) ABSTRACT

The present invention relates to a lactic acid bacterium, in particular a strain of the *Streptococcus* genus, with reduced sensitivity to cos-type bacteriophages. The invention also relates to methods to engineer these lactic acid bacteria as well as their use to ferment milk.

8 Claims, No Drawings

Specification includes a Sequence Listing.

(56) References Cited

OTHER PUBLICATIONS

Tremblay et al., Complete Genomic Sequence of the Lytic Bacteriophage DT1 of *Streptococcus thermophilus*, Virology, 255, Mar. 1999,63-76.
Varghese, SER62871, *Streptococcus gallolyticus* methionine aminopeptidase, XP00279195, Oct. 2016, 1 p.
Barrangou et al., CRISPR Provides Acquired Resistance Against Viruses in Prokaryotes, Science, 315, Mar. 2007,1709-1712.
Horvath et al., Diversity, Activity, and Evolution of CRISPR Loci in *Streptococcus thermophilus*, Journal of Bacteriology, vol. 190, No. 4, Feb. 2008, 1401-1412.
Labrie et al., Complete Genome Sequence of *Streptococcus thermophilus* SMQ-301, a Model Strain for Phage-Host Interactions, Genome Announcements, vol. 3, Issue 3, May/Jun. 2015, 1-2.
Félix d'Hérelle Reference Centre for Bacterial Viruses (www.phage.ulaval.ca) under reference HER 1368, Accession No. CP011217.1, 2 pgs., retrieved from the Internet Aug. 2021.
Félix d'Hérelle Reference Centre for Bacterial Viruses, under reference HER 368, Accession No. NC_002072.2, 3 pgs., retrieved from the Internet Aug. 2021.
Félix d'Hérelle Reference Centre for Bacterial Viruses, under reference HER503, Reference HER1503, 2 pgs., retrieved from the Internet Aug. 2021.
Le Marrec et al., Two Groups of Bacteriophages Infecting *Streptococcus thermophilus* Can Be Distinguished on the Basis of Mode of Packaging and Genetic Determinants for Major Structural Proteins, Applied and Environmental Microbiology, vol. 63, No. 8, Aug. 1997, 3426-3253.
Delisle et al., Biology and Genome Sequence of *Streptococcus mutans* Phage M102AD, Applied and Environmental Microbiology, vol. 78, No. 7, Apr. 2012, 2264-2271.
Beaucage et al., Deoxynucleoside Phosphoramidites—A New Class Of Key Intermediates For Deoxypolynucleotide Synthesis, Tetrahedron Letters 22, 1981, 1859-1869.
Higgins et al., CLUSTAL: a package for performing multiple sequence alignment on a microcomputer, Gene 73(1), Aug. 1988, 237-244.
De Vos, Gene Cloning and expression in lactic streptococci, FEMS Microbiology Reviews, 46, Sep. 1987, 281-295.
Bissonnette et al., Characterization of Mesophilic Mixed Starter Cultures Used for the Manufacture of Aged Cheddar Cheese, J. Dairy Sci., 83, Apr. 2000, 620-627.
Li et al., The Sequence Alignment/Map format SAMtools, Bioinformatics, Applications Note, vol. 25, No. 16, Aug. 2009, 2078-2079.
Gibson et al., Enzymatic assembly of DNA molecules up to several hundred kilobases, Nature Methods, vol. 6, No. 5, May 2009, 343-346.
Gardan et al., The Oligopeptide Transport System Is Essential for the Development of Natural Competence in *Streptococcus thermophilus* Strain LMD-9, Journal of Bacteriology, vol. 191, No. 14, Jul. 2009, 4647-4655.
Hynes et al., An anti-CRISPR from a virulent streptococcal phage inhibits *Streptococcus pyogenes* Cas9, Nature Microbiology, vol. 2, Oct. 2017, 1374-1380.
Kropinski et al., Enumeration of Bacteriophages by Double Agar Overlay Plaque Assay, Clokie M.R., Kropinski A. M. (eds) Bacteriophages. Methods in Molecular Biology™, vol. 501., Chapt. 7, 2009, Humana Press., 69-76.
Caruthers et al., "New chemical methods for synthesizing polynucleotides", Nucleic Acids Research, Symposium Series No. 7, 1980, pp. 215-223.
Horn et al., "Synthesis of olignonucleotides on cellulose. Part II: design and synthetic strategy to the synthesis of 22 bligodeoxynucleotides coding for Gastric Inhibitory Polypeptide (GIP)", Nucleic Acids Research, Symposium Series No. 7, 1980, pp. 225-232.

\* cited by examiner

LACTIC ACID BACTERIUM WITH A REDUCTION OF SENSITIVITY TO COS-TYPE BACTERIOPHAGES

CROSS-REFERENCE TO RELATED APPLICATIONS

This application is a U.S. national stage application under 35 U.S.C. § 371 of International Application No. PCT/EP2020/053676, filed on Feb. 13, 2020, entitled "LACTIC ACID BACTERIUM WITH A REDUCTION OF SENSITIVITY TO COS-TYPE BACTERIOPHAGES," and claims priority from U.S. provisional application No. 62/805,388, entitled "LACTIC ACID BACTERIUM WITH A REDUCTION OF SENSITIVITY TO COS-TYPE BACTERIOPHAGES," filed Feb. 14, 2019, and claims priority from U.S. provisional application No. 62/904,787, entitled "LACTIC ACID BACTERIUM WITH A REDUCTION OF SENSITIVITY TO COS-TYPE BACTERIOPHAGES," filed Sep. 24, 2019, the contents of which are incorporated by reference in their entirety.

INCORPORATION BY REFERENCE OF THE SEQUENCE LISTING

The present application is being filed with a Sequence Listing in electronic format. The Sequence Listing is provided as a file entitled NB41022USPCT_SeqList.txt, created on Aug. 4, 2021, which is 51,450 bytes in size. The information in the electronic format of the Sequence Listing is incorporated by reference in its entirety.

FIELD OF THE INVENTION

The present invention relates to a lactic acid bacterium with reduced sensitivity to cos-type bacteriophages.

BACKGROUND TO THE INVENTION

Lactic acid bacterial starter cultures are used extensively in the food industry for the manufacture of fermented products including dairy products (such as yoghurt, butter and cheese), meat products, bakery products, wine and vegetable products. Among the lactic acid bacteria widely used in the food industry, examples include the genera *Streptococcus, Lactococcus, Lactobacillus, Leuconostoc, Pediococcus, Enterococcus, Oenococcus* and *Bifidobacterium*. For example, the lactic acid bacterium *Streptococcus thermophilus* is extensively used by the dairy industry. The preparation of cultures is labour intensive, occupies a large amount of space and equipment, and there is a considerable risk of contamination with bacteriophages (phages) during milk fermentation.

The attack of bacterial cultures by bacteriophage infection and multiplication is considered to be one of the major problems of the industrial use of bacterial cultures. There are many different types of phages with varying mechanisms to attack bacteria. Moreover, new strains of bacteriophages emerge. Many different strains of bacteriophages that can infect bacterial strains used in the industry, including species of lactic acid bacteria, for example *Lactococcus lactis* and *Streptococcus thermophilus*, have been found and isolated.

Strategies used in the industry to minimise bacteriophage infection, and thus failure of a bacterial culture, are not fully effective. Such strategies include the use of mixed starter cultures to ensure that a certain level of resistance to phage attack is present. In addition, rotation of selected bacterial strains which are sensitive to different bacteriophages is used. However, rapid replacement of the bacterial strain with a resistant strain following the emergence of a new phage is usually not possible. Therefore, it has not yet been possible to eliminate phage contamination in the food industry.

The lytic infection cycle of bacteriophages notably involves phage adsorption to the bacterial host cell surface, injection of phage DNA into the cell, phage DNA replication, phage protein expression, phage assembly and host bacterial cell lysis to release the newly assembled phage particles. Bacterial phage resistance mechanisms depend upon host factors involved in one or more steps of the lytic cycle of phage replication and are generally classified based on the step of the infectious cycle they interfere with.

While numerous phage resistance mechanisms have been found in other bacterial species, only a few have been identified in *S. thermophilus*. The most dominant defence mechanisms in this species are the CRISPR-Cas systems (Barrangou et al., 2007; Horvath et al., 2008). In this defence mechanism, the bacterial cell accumulates short sequences, named spacers, from the phage genomes which act as the cell's memory of previous encounters and serve as guides for specific cleavage of invading phage DNA. Little information is available about other host factors involved in phage infection in this food-grade streptococcal species.

There is a continuing need in the art to provide improved bacterial strains for use in the food or feed industry—such as bacterial strains that have a reduced sensitivity to phages. There is therefore a need to identify host factors involved in phage infection in lactic acid bacteria, for example in the genus *Streptococcus*.

SUMMARY OF THE INVENTION

The present inventors have surprisingly found that a host gene coding for methionine aminopeptidase (MetAP protein) is involved in phage infection and is necessary for cos-type phage DT1 to complete its lytic cycle. Mutation in the metAP gene provides *Streptococcus thermophilus* with reduced sensitivity to cos-type phages. Complementation of the mutated strains with the metAP gene of a sensitive strain results in restoration of the phage sensitivity phenotype. Introducing the same mutation in a *Streptococcus mutans* strain also provides a reduced phage-sensitivity phenotype suggesting the wide-ranging importance of the host MetAP in phage infection. The inventors have also shown that the phenotype of reduced sensitivity to cos-type phages is stable over time (at least 60 generations), confirming the stability of the metAP mutations and the interest of metAP-mutated lactic acid bacteria in industrial fermentation.

In an aspect, the invention is directed to a lactic acid bacterium comprising a MetAP$^R$ allele encoding a methionine aminopeptidase protein (MetAP$^R$ protein), wherein said MetAP$^R$ allele reduces the sensitivity to phage DT1 when inserted in lieu of the allele of the metAP gene of *Streptococcus thermophilus* SMQ-301 strain, wherein sensitivity to phage DT1 is determined by Efficiency of Plaquing (EOP) Assay I. Thus, the invention is directed to a lactic acid bacterium comprising a MetAP$^R$ allele encoding a methionine aminopeptidase (MetAP$^R$ protein) protein, wherein said MetAP$^R$ allele is defined as a metAP allele which reduces the sensitivity to phage DT1 of a *Streptococcus thermophilus* SMQ-301 derivative strain, said SMQ-301 derivative strain being a *Streptococcus thermophilus* SMQ-301 strain into which its metAP allele has been replaced by said MetAP$^R$ allele, and wherein sensitivity to phage DT1 is determined by Efficiency of Plaquing (EOP) Assay I. In a particular embodiment, said lactic acid bacterium is a strain of the *Streptococcus* genus selected from the group consisting of a *Streptococcus thermophilus* strain or a *Streptococcus mutans* strain.

In an aspect, the invention is directed to a bacterial composition comprising the lactic acid bacterium of the invention.

In an aspect, the invention is directed to a food or feed product comprising the lactic acid bacterium or the bacterial composition of the invention.

In an aspect, the invention is directed to a method for manufacturing a fermented product, comprising: a) inoculating a substrate with the lactic acid bacterium or the bacterial composition of the invention, and b) fermenting the inoculated substrate obtained from step a) to obtain a fermented product, preferably a fermented dairy product.

In an aspect, the invention is directed to the use of the lactic acid bacterium or the bacterial composition of the invention, to manufacture a food or feed product, preferably a fermented food product, more preferably a fermented dairy product.

In an aspect, the invention is directed to a polynucleotide encoding a MetAP$^R$ protein, wherein said polynucleotide reduces the sensitivity to phage DT1 when inserted in lieu of the allele of the metAP gene of *Streptococcus thermophilus* SMQ-301 strain, wherein sensitivity to phage DT1 is determined by Efficiency of Plaquing (EOP) Assay I. Thus, the invention is directed to a polynucleotide encoding a MetAP$^R$ protein, wherein said polynucleotide is a metAP allele which reduces the sensitivity to phage DT1 of a *Streptococcus thermophilus* SMQ-301 derivative strain, said SMQ-301 derivative strain being a *Streptococcus thermophilus* SMQ-301 strain into which its metAP allele has been replaced by said metAP$^R$ allele, and wherein sensitivity to phage DT1 is determined by Efficiency of Plaquing (EOP) Assay I.

In an aspect, the invention is directed to the use of a polynucleotide of the invention, to reduce the sensitivity to at least one cos-type phage of a lactic acid bacterium sensitive to cos-type phages, wherein sensitivity to at least one cos-type phage is determined by EOP Assay I.

In an aspect, the invention is directed to a method to prepare a lactic acid bacteria strain having a reduced sensitivity to at least one cos-type phage, comprising: a) providing a lactic acid bacteria strain sensitive to cos-type phages; b) replacing the allele of the metAP gene of said lactic acid bacteria strain sensitive to cos-type phages with a polynucleotide of the invention, or modifying the sequence of the metAP gene of a lactic acid bacteria strain sensitive to cos-type phages to have a metAP allele with the same sequence as a polynucleotide of the invention; and c) recovering the lactic acid bacteria strain(s) having a reduced sensitivity to at least one cos-type phage, wherein sensitivity to at least one cos-type phage is determined by EOP Assay I.

In an aspect, the invention is directed to a method to identify a MetAP$^R$ allele encoding a MetAP$^R$ protein, comprising: a) inserting the metAP allele to be tested in lieu of the allele of the metAP gene of *Streptococcus thermophilus* SMQ-301 strain, to obtain a SMQ-301 derivative strain; and b) determining by Efficiency of Plaquing Assay I the EOP of phage DT1 on the SMQ-301 derivative strain of step a), wherein an EOP reduction of at least 4 log, of at least 5 log or of at least 6 log is indicative of a metAP allele which is a MetAP$^R$ allele encoding a MetAP$^R$ protein.

DETAILED DESCRIPTION OF THE INVENTION

General Definitions

Unless defined otherwise, all technical and scientific terms used herein have the same meaning as commonly understood by one of ordinary skill in the art to which this disclosure belongs.

This disclosure is not limited by the exemplary methods and materials disclosed herein, and any methods and materials similar or equivalent to those described herein can be used in the practice or testing of embodiments of this disclosure.

The headings provided herein are not limitations of the various aspects or embodiments of this disclosure which can be used by reference to the specification as a whole. Accordingly, the terms defined immediately below are more fully defined by reference to the specification as a whole.

As used herein, the term "polynucleotide" is synonymous with the term "nucleotide sequence" and/or the term "nucleic acid sequence". Unless otherwise indicated, any nucleic acid sequences are written left to right in 5' to 3' orientation.

The term "protein", as used herein, includes proteins, polypeptides, and peptides. As used herein, the term "amino acid sequence" is synonymous with the term "protein". In the present disclosure and claims, the name of the amino acid, the conventional three-letter code or the conventional one-letter code for amino acid residues is used. It is also understood that a protein may be coded for by more than one nucleotide sequence due to the degeneracy of the genetic code. Unless otherwise indicated, any amino acid sequences are written left to right in amino to carboxy orientation.

In the present invention, a specific numbering of amino acid residue positions in the MetAP$^R$ protein may be employed. By alignment of the amino acid sequence of a sample MetAP protein with the MetAP protein of SEQ ID NO: 2 it is possible to allot a number to an amino acid residue position in said sample MetAP protein which corresponds to the amino acid residue position or numbering of the amino acid sequence shown in SEQ ID NO: 2 of the present invention.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

It must be noted that as used herein and in the appended claims, the singular forms "a", "an", and "the" include plural referents unless the context clearly dictates otherwise. The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The publications discussed herein are provided solely for their disclosure prior to the filing date of the present application. Nothing herein is to be construed as an admission that such publications constitute prior art to the claims appended hereto.

The present inventors have surprisingly found that a host gene coding for methionine aminopeptidase (MetAP) is a bacterial host factor involved in cos-type phage multiplication in *Streptococcus* strains. In particular, the present inventors have surprisingly found that a MetAP$^R$ allele, encoding a MetAP$^R$ protein, reduces the sensitivity of *Streptococcus* strains to at least one cos-type phage.

In an aspect, the present invention provides a method to identify a MetAP$^R$ allele encoding a MetAP$^R$ protein, comprising:
  a) inserting the metAP allele to be tested (candidate metAP allele) in lieu of the allele of the metAP gene of *Streptococcus thermophilus* SMQ-301, to obtain a SMQ-301 derivative strain; and
  b) determining by Efficiency of Plaquing Assay I the EOP of phage DT1 on the SMQ-301 derivative strain of step a),
  wherein an EOP reduction of at least 4 log is indicative of a metAP allele which is a metAP$^R$ allele encoding a MetAP$^R$ protein.

As used herein, the expression "an allele of the metAP gene" means the version of the metAP gene found in a particular lactic acid bacterium. As for most of the bacterial genes, the nucleotide sequence of a gene can vary, and alleles represent the different sequences of the same gene. Thus, the allele of the metAP gene of *Streptococcus thermophilus* SMQ-301 is as set forth in SEQ ID NO:1. This allele as defined in SEQ ID NO:1 encodes a MetAP protein as set forth in SEQ ID NO:2.

MetAP$^R$ Alleles Encoding MetAP$^R$ Protein

The inventors have shown that some of these metAP alleles are able to reduce the sensitivity of *Streptococcus thermophilus* SMQ-301 to phage DT1 when they are inserted in lieu of the original (i.e., native) allele of the metAP gene (SEQ ID NO:1) of SMQ-301. These metAP alleles are defined herein as "MetAP$^R$ alleles". The protein encoded by these metAP$^R$ alleles is referred herein as "MetAP$^R$ protein".

Thus, any MetAP$^R$ allele (encoding a MetAP$^R$ protein) reducing the sensitivity of the SMQ-301 strain to phage DT1 (as defined herein) is part of the invention. In other words, a metAP$^R$ allele is defined as a metAP allele which reduces the sensitivity to phage DT1 of a *Streptococcus thermophilus* SMQ-301 derivative strain, said SMQ-301 derivative strain being a *Streptococcus thermophilus* SMQ-301 strain into which its original metAP allele has been replaced by said MetAP$^R$ allele.

In an embodiment, a MetAP$^R$ allele is defined herein (in particular in the context of a lactic acid bacterium or a polynucleotide of the invention) as a metAP allele identified by the following method:
  a) inserting the metAP allele to be tested (candidate metAP allele) in lieu of the allele of the metAP gene of *Streptococcus thermophilus* SMQ-301 (as set forth in SEQ ID NO:1), to obtain a SMQ-301 derivative strain; and
  b) determining by Efficiency of Plaquing Assay I the EOP of phage DT1 on the SMQ-301 derivative strain of step a),
  wherein an EOP reduction of at least 4 log is indicative of a metAP allele which is a metAP$^R$ allele encoding a MetAP$^R$ protein.

Non-limitative examples of MetAP$^R$ proteins are disclosed below.

One way to determine the reduction of sensitivity to bacteriophage conferred by a metAP$^R$ allele of the invention is to determine the efficiency of plaquing (EOP) of a phage on a *Streptococcus* strain in which the candidate metAP allele of the invention has been inserted in lieu of the original allele of the metAP gene of this *Streptococcus* strain.

In an embodiment, the reduction of sensitivity is determined by calculating the efficiency of plaquing (EOP) in the Efficiency of Plaquing Assay I (EOP Assay I) described herein.

Efficiency of Plaquing Assay I

One way to determine the reduced sensitivity to cos-type bacteriophage(s) conferred by a candidate metAP allele is to determine the sensitivity of both a lactic acid bacterium sensitive to cos-type phages (called herein "reference strain") and the corresponding derivative lactic acid bacterium in which the allele of its metAP gene has been replaced with a candidate metAP allele (called herein "derivative strain").

The bacteriophage sensitivity of a lactic acid bacterium of the invention (in particular of the *Streptococcus* genus, in particular of a *Streptococcus thermophilus* strain) can be determined by calculating the efficiency of plaquing (EOP) in the Efficiency of Plaquing Assay I (EOP assay I) described herein.

The numeration of infectious phage particles is performed using the double agar overlay plaque assay as described by Kropinski et al. 2009, named "Efficiency of Plaquing Assay I" herein. The method consists in infecting a lawn of bacteria growing on the surface in a soft-agar nutritive medium. Infection by a phage will result in a localized clear or translucent zone corresponding to the area where bacterial are killed or are not growing, termed plaques. The infectious phage unit is thus termed plaque-forming unit (pfu). Because the numeration of phages using the assay necessitates a minimum of 30 to a maximum of 300 pfu per plate, the phage suspension may require dilution. For this purpose, the primary phage suspension is serially 10-fold diluted in 10 mL of M17 medium containing 5 g/L of lactose (v/v).

The Efficiency of Plaquing Assay I has the following steps:
  i. pre-cultivate each of the strains to be tested (the reference strain and its derivative strain(s) to be tested as defined herein) in M17 medium containing 5 g/L of lactose (v/v) overnight at 37° C.;
  ii. use each pre-culture separately to seed at 1% (v/v) 5 mL of melted M17-CaCl$_2$ soft-agar medium containing 5 g/L of lactose, 10 mM of CaCl$_2$ and 5 g/L (w/v) of agar (that is kept at 47° C. in a water bath);
  iii. add 100 µL of the phage dilution to be tested to each of the seeded media;
  iv. after mixing, pour each of the mixtures onto the surface of a M17-CaCl$_2$ solid-agar medium containing 5 g/L of lactose, 10 mM of CaCl$_2$ and 15 g/L (w/v) of agar;
  v. after the solidification of the overlay, incubate the plates inverted for 48 hours at 37° C.;
  vi. enumerate plaques (on plates presenting 30 to 300 plaques);
  vii. calculate the titre of virulent phages as: the number of plaques×10× the reciprocal of the dilution rate; and express in pfu/mL; and
  viii. calculate the EOP of the phage on a derivative strain as the titre of the phage on the derivative strain to be tested divided by the titre of the phage on the reference strain (wherein the EOP of the reference strain is 1).

In a particular embodiment, said lactic acid bacterium of the invention is a strain of the genus *Streptococcus*. The sensitivity to bacteriophage conferred by a candidate metAP allele is determined by the Efficiency of Plaquing Assay I described herein, using a strain of the *Streptococcus* genus sensitive to cos-type phages (reference strain) and the corresponding derivative strain of the *Streptococcus* genus in which the allele of its metAP gene has been replaced with a candidate metAP allele.

In a particular embodiment, said lactic acid bacterium of the invention is of the species *Streptococcus thermophilus*. The sensitivity to bacteriophage conferred by a candidate metAP allele is determined by the Efficiency of Plaquing Assay I described herein, using a *Streptococcus thermophilus* strain sensitive to cos-type phages (reference strain) and the corresponding derivative *Streptococcus thermophilus* strain in which the allele of its metAP gene has been replaced with a candidate metAP allele.

To determine whether a candidate metAP allele is a MetAP$^R$ according to the invention, the *Streptococcus thermophilus* strain SMQ-301 is used as the "reference strain", and the *Streptococcus thermophilus* strain obtained by the insertion of a candidate metAP allele in lieu of the allele of the metAP gene of the *Streptococcus thermophilus* SMQ-301 strain is used as a derivative strain (called herein "a SMQ-301 derivative").

Thus, in an embodiment, the Efficiency of Plaquing Assay I as defined herein is implemented with:

the *Streptococcus thermophilus* strain SMQ-301 as the "reference strain"; the SMQ-301 strain is commercially available and used as a model organism to study phage-host interactions (Tremblay and Moineau, 1999; Labrie et al., 2015), and is available at Félix d'Hérelle Reference Centre for Bacterial Viruses (www.phage.ulaval.ca) under reference HER 1368; the genome sequence of this strain is available under accession number CP011217.1;

the *Streptococcus thermophilus* strain SMQ-301 into which the allele of its metAP gene has been replaced by the candidate metAP allele (SMQ-301 derivative strain); thus, the allele of the metAP gene of the SMQ-301 derivative strain does not encode a MetAP protein as set forth in SEQ ID NO:2, in particular is not as set forth in SEQ ID NO:1; and the phage DT1, which is commercially available (Tremblay and Moineau 1999; Labrie et al., 2015) and available at the Félix d'Hérelle Reference Centre for Bacterial Viruses, under reference HER 368; the genome sequence of this phage is available under accession number NC_002072.2.

As defined herein, a candidate metAP allele is considered to be a MetAP$^R$ allele according to the invention, when said candidate metAP allele reduces the sensitivity to phage DT1 when inserted in lieu of the allele of the metAP gene of *Streptococcus thermophilus* SMQ-301 strain, wherein sensitivity to phage DT1 is determined by Efficiency of Plaquing (EOP) Assay I. Thus, a candidate metAP allele is considered to be a MetAP$^R$ allele according to the invention, when said candidate metAP allele reduces the sensitivity to phage DT1 of a *Streptococcus thermophilus* SMQ-301 derivative strain, said SMQ-301 derivative strain being a *Streptococcus thermophilus* SMQ-301 strain into which its original metAP allele has been replaced by said MetAP$^R$ allele, and wherein sensitivity to phage DT1 is determined by Efficiency of Plaquing (EOP) Assay I.

It is noteworthy that the insertion of a candidate metAP allele (including a MetAP$^R$ allele of the invention or a metAP variant allele as defined herein) in lieu of the original allele of the metAP gene of the *Streptococcus thermophilus* SMQ-301 must lead to a SMQ-301 derivative strain which can be tested by the Efficiency of Plaquing (EOP) Assay I. Any metAP allele, the sequence of which renders the application of the EOP assay I and the determination of the sensitivity to DT1 not possible, is not considered as a metAP allele as defined herein.

By "reduction of the sensitivity to phage DT1" by EOP Assay I, it is meant an EOP reduction of at least 4 log. In an embodiment, the EOP reduction is of at least 5 log. In an embodiment, the EOP reduction is of at least 6 log. In an embodiment, the EOP reduction is of at least 7 log. In an embodiment, the EOP reduction is of at least 8 log. In an embodiment, a metAP allele is considered to be a MetAP$^R$ allele according to the invention, when the EOP reduction is selected from the group consisting of EOP reduction of at least 4 log, at least 5 log, at least 6 log, at least 7 log and at least 8 log, wherein sensitivity to phage DT1 is determined by Efficiency of Plaquing (EOP) Assay I. Thus, a candidate metAP allele is considered to be a MetAP$^R$ allele according to the invention, when said candidate metAP allele reduces the sensitivity to phage DT1 of a *Streptococcus thermophilus* SMQ-301 derivative strain of at least 4 log, said SMQ-301 derivative strain being a *Streptococcus thermophilus* SMQ-301 strain into which its metAP allele has been replaced by said MetAP$^R$ allele, and wherein sensitivity to phage DT1 is determined by Efficiency of Plaquing (EOP) Assay I (i.e., as compared to *Streptococcus thermophilus* SMQ-301 strain)

In contrast, a candidate metAP allele which, when inserted in lieu of the allele of the metAP gene of *Streptococcus thermophilus* SMQ-301 strain does not reduce the EOP of at least 4 log—wherein sensitivity to phage DT1 is determined by Efficiency of Plaquing (EOP) Assay I—is not considered to be a MetAP$^R$ allele according to the invention. Thus, a candidate metAP allele which does not reduce the EOP of phage DT1 on a *Streptococcus thermophilus* SMQ-301 derivative strain of at least 4 log, said SMQ-301 derivative strain being a *Streptococcus thermophilus* SMQ-301 strain into which its metAP allele has been replaced by said candidate metAP allele, and wherein sensitivity to phage DT1 is determined by Efficiency of Plaquing (EOP) Assay I, is not considered to be a MetAP$^R$ allele according to the invention.

The expression "reduce the sensitivity" or "reduce the EOP" is defined according to assay I, i.e., by determining the EOP of phage DT1 on the *Streptococcus thermophilus* SMQ-301 derivative strain and comparing it to the EOP of phage DT1 on *Streptococcus thermophilus* SMQ-301 strain.

metAP Variant Allele Encoding a MetAP Variant Protein

A metAP candidate allele, which 1) encodes a MetAP protein the sequence of which has at least 80% identity with SEQ ID NO:2, and 2) does not reduce the EOP or reduces the EOP of less than 3 log—wherein sensitivity to phage DT1 is determined by Efficiency of Plaquing (EOP) Assay I, is referred herein as a metAP variant allele (encoding a MetAP variant protein). The expression "metAP variant protein" is used interchangeably with the expression "metAP variant protein having at least 80% identity with SEQ ID NO:2".

In an embodiment, a metAP variant allele, when inserted in lieu of the allele of the metAP gene of *Streptococcus thermophilus* SMQ-301 strain, reduces the EOP of less than 3 log—wherein sensitivity to phage DT1 is determined by Efficiency of Plaquing (EOP) Assay I. Thus, a metAP variant allele reduces the EOP of phage DT1 on a *Streptococcus thermophilus* SMQ-301 derivative strain, of less than 3 log, said SMQ-301 derivative strain being a *Streptococcus thermophilus* SMQ-301 strain into which its metAP allele has been replaced by said metAP variant allele and wherein sensitivity to phage DT1 is determined by Efficiency of Plaquing (EOP) Assay I. In an embodiment, the EOP reduction is less than 3 log. In an embodiment, the EOP reduction is less than 2 log. In an embodiment, the EOP reduction is less than 3 log or less than 2 log.

In an embodiment, a metAP variant allele, when inserted in lieu of the allele of the metAP gene of *Streptococcus thermophilus* SMQ-301 strain, leads to the same EOP—wherein sensitivity to phage DT1 is determined by Efficiency of Plaquing (EOP) Assay I. Thus, a metAP variant allele leads to the same EOP of phage DT1 on *Streptococcus thermophilus* SMQ-301 derivative strain as that of phage DT1 on *Streptococcus thermophilus* SMQ-301 strain, said SMQ-301 derivative strain being a *Streptococcus thermophilus* SMQ-301 strain into which its metAP allele has been replaced by said metAP variant allele, and wherein sensitivity to phage DT1 is determined by Efficiency of Plaquing (EOP) Assay I.

In combination with any of the embodiments directed to EOP reduction above, a metAP variant allele is also defined as encoding a MetAP variant protein, the sequence of which is at least 80% identical to SEQ ID NO:2. By "at least 80% identical to SEQ ID NO:2", it is meant at least 80%, at least 85%, at least 90%, at least 95%, at least 96%, at least 97%, at least 98% or at least 99%. In an embodiment, a MetAP variant protein (encoded by a metAP variant allele) has a sequence which is at least 85% identical to SEQ ID NO:2. In an embodiment, a MetAP variant protein (encoded by a metAP variant allele) has a sequence which is at least 85% identical to SEQ ID NO:2. In an embodiment, a MetAP variant protein (encoded by a metAP variant allele) has a sequence which is at least 90% identical to SEQ ID NO:2. In an embodiment, a MetAP variant protein (encoded by a metAP variant allele) has a sequence which is at least 95% identical to SEQ ID NO:2. In an embodiment, a MetAP variant protein (encoded by a metAP variant allele) has a sequence which is at least 96% identical to SEQ ID NO:2. In an embodiment, a MetAP variant protein (encoded by a metAP variant allele) has a sequence which is at least 97% identical to SEQ ID NO:2. In an embodiment, a MetAP variant protein (encoded by a metAP variant allele) has a sequence which is at least 98% identical to SEQ ID NO:2. In an embodiment, a MetAP variant protein (encoded by a metAP variant allele) has a sequence which is at least 99% identical to SEQ ID NO:2.

In an embodiment, in combination with the percentage of identity, the size of the MetAP variant protein is the same as the MetAP protein as defined in SEQ ID NO:2 (286 amino acid residues); thus, in an embodiment, a metAP variant allele is additionally defined as encoding a 286-amino acid MetAP variant protein.

In an embodiment, a metAP variant allele is defined herein as:
1) encoding a MetAP variant protein, the sequence of which is at least 80%, at least 85%, at least 90%, at least 95%, at least 96%, at least 97%, at least 98% or at least 99% identical to SEQ ID NO:2; and
2) when inserted in lieu of the allele of the metAP gene of *Streptococcus thermophilus* SMQ-301 strain, reducing the EOP of less than 3 log or less than 2 log, wherein sensitivity to phage DT1 is determined by Efficiency of Plaquing (EOP) Assay I.

Thus, a metAP variant allele is defined herein as:
1) encoding a MetAP variant protein, the sequence of which is at least 80%, at least 85%, at least 90%, at least 95%, at least 96%, at least 97%, at least 98% or at least 99% identical to SEQ ID NO:2; and
2) reducing the EOP of phage DT1 on a *Streptococcus thermophilus* SMQ-301 derivative strain of less than 3 log, said SMQ-301 derivative strain being a *Streptococcus thermophilus* SMQ-301 strain into which its metAP allele has been replaced by said metAP variant allele, and wherein sensitivity to phage DT1 is determined by Efficiency of Plaquing (EOP) Assay I, In an embodiment, a metAP variant allele is defined herein as:
1) encoding a MetAP variant protein, the sequence of which is at least 80%, at least 85%, at least 90%, at least 95%, at least 96%, at least 97%, at least 98% or at least 99% identical to SEQ ID NO:2; and
2) when inserted in lieu of the allele of the metAP gene of *Streptococcus thermophilus* SMQ-301 strain, leading to the same EOP—wherein sensitivity to phage DT1 is determined by Efficiency of Plaquing (EOP) Assay I.

Thus, a metAP variant allele is also defined herein as:
1) encoding a MetAP variant protein, the sequence of which is at least 80%, at least 85%, at least 90%, at least 95%, at least 96%, at least 97%, at least 98% or at least 99% identical to SEQ ID NO:2; and
2) leads to the same EOP of phage DT1 on a *Streptococcus thermophilus* SMQ-301 derivative strain as that of phage DT1 on *Streptococcus thermophilus* SMQ-301 strain, said SMQ-301 derivative strain being a *Streptococcus thermophilus* SMQ-301 strain into which its metAP allele has been replaced by said metAP variant allele, and wherein sensitivity to phage DT1 is determined by Efficiency of Plaquing (EOP) Assay I.

metAP variant alleles as defined herein can easily be identified by the person skilled in the art, starting from *Streptococcus thermophilus* strains which are known or can be characterized as being sensitive to the phage DT1 (wherein sensitivity to phage DT1 is determined by EOP Assay I).

The expression "same EOP" or "reduced EOP of less than 3 log or less than 2 log" is defined according to assay I, i.e., by determining the EOP of phage DT1 on the *Streptococcus thermophilus* SMQ-301 derivative strain and comparing it to the EOP of phage DT1 on *Streptococcus thermophilus* SMQ-301 strain.

Replacement of the Allele of the metAP Gene of a Lactic Acid Bacterium (in Particular of the SMQ-301 Strain)

The replacement of the allele of the metAP gene of a reference lactic acid bacterium (in particular of a strain of the *Streptococcus* genus, in particular of a *Streptococcus thermophilus* strain) by a metAP allele (such as a candidate metAP allele or metAP variant allele) is carried out using conventional techniques in molecular biology and is within the capabilities of a person of ordinary skill in the art. Generally speaking, suitable routine methods include replacement via homologous recombination.

The expression "metAP allele inserted in lieu of the allele of the metAP gene" is synonymous to the expression "the allele of the metAP gene is replaced by a metAP allele" (such as a candidate metAP allele or a metAP variant allele). The expression "MetAP$^R$ allele inserted in lieu of the allele of the metAP gene" is synonymous to the expression "the allele of the metAP gene is replaced by a MetAP$^R$ allele".

Replaced (or inserted in lieu) means that the sequence of the MetAP protein encoded by the metAP allele to be inserted (in particular a candidate metAP allele or metAP variant allele) is different from the sequence of the MetAP protein encoded by the allele of the metAP gene of the original strain (such as a reference strain). Thus, replaced (or inserted in lieu) means that the coding sequence of the metAP gene of the original strain (from the 1$^{st}$ nucleotide of the start codon to the last nucleotide of the stop codon) is replaced by the corresponding coding sequence of the metAP allele (in particular of the candidate metAP allele or the metAP variant allele).

In the case of the SMQ-301 strain, replaced (or inserted in lieu) means that the sequence of the MetAP protein encoded by the metAP allele to be inserted (in particular a candidate metAP allele or metAP variant allele) is different from the sequence of the MetAP protein encoded by the original metAP gene of the SMQ-301 strain. Thus, replaced (or inserted in lieu) means that the coding sequence of the metAP gene of the SMQ-301 strain (from the 1$^{st}$ nucleotide of the start codon to the last nucleotide of the stop codon, i.e., nucleotides 1 to 861 of SEQ ID NO:1) is replaced by the corresponding coding sequence of the metAP allele (in particular of the candidate metAP allele or the metAP variant allele).

To Generate a Candidate metAP Allele

Candidate metAP alleles can be generated by random or directed mutagenesis, starting from a metAP allele which is not a MetAP$^R$ allele, in particular starting from a metAP allele encoding the MetAP protein as defined in SEQ ID NO:2 (such as SEQ ID NO:1) or from a MetAP variant allele as defined herein. In an embodiment, candidate metAP alleles are generated by random mutagenesis. In another embodiment, candidate metAP alleles can be generated by directed mutagenesis. Suitable mutagenesis protocols for random or directed mutagenesis are described in the material and methods section below.

Candidate metAP alleles can also be generated by submitting a *Streptococcus thermophilus* bacterium, the allele of its metAP gene is not a MetAP$^R$ allele (such as the SMQ-301 strain), to a challenge by the phage DT1. A suitable protocol for challenging a strain with a phage is described in the material and methods section below. In an embodiment, to decrease the number of genetic events leading to a reduced sensitivity to phages due to the CRISPR-Cas systems (and thus to increase the number of genetic events linked to metAP mutation), it is possible to inhibit or decrease the efficiency of the CRISPR-Cas systems by using phages bearing anti-CRISPR gene(s) (acr genes) (WO2018/197495).

The candidate metAP alleles thus generated can be screened using the method to identify a MetAP$^R$ allele as defined herein.

In an aspect, the present invention provides a lactic acid bacterium comprising a metAP$^R$ allele (encoding a MetAP$^R$ protein), wherein said MetAP$^R$ allele reduces the sensitivity to phage DT1 when inserted in lieu of the allele of the metAP gene of *Streptococcus thermophilus* SMQ-301 strain, wherein sensitivity to phage DT1 is determined by Efficiency of Plaquing (EOP) Assay I. Thus, the invention is directed to a lactic acid bacterium comprising a MetAP$^R$ allele encoding a methionine aminopeptidase (MetAP$^R$ protein) protein, wherein said MetAP$^R$ allele is defined as a metAP allele which reduces the sensitivity to phage DT1 of a *Streptococcus thermophilus* SMQ-301 derivative strain, said SMQ-301 derivative strain being a *Streptococcus thermophilus* SMQ-301 strain into which its (original) metAP allele has been replaced by said MetAP$^R$ allele, and wherein sensitivity to phage DT1 is determined by Efficiency of Plaquing (EOP) Assay I. The MetAP$^R$ allele is as generated, as screened and/or as defined herein. The expression "reduces the sensitivity to phage DT1" is as defined herein for the definition of the MetAP$^R$ allele. In particular and as defined herein, the reduction of sensitivity to phage DT1 linked to the MetAP$^R$ allele of the invention is of at least 4 log, determined by Efficiency of Plaquing (EOP) Assay I.

It is noteworthy that the expression "comprising a MetAP$^R$ allele" means that the sole allele of the metAP gene contained in the genome of the lactic acid bacterium (LAB) is a metAP$^R$ allele. Thus, the allele of the metAP gene of the LAB of the invention is a MetAP$^R$ allele as defined herein. It is not contemplated that the LAB of the invention comprises several alleles of the metAP gene. In an embodiment, the LAB of the invention comprises, as the sole allele of its metAP gene, a MetAP$^R$ allele which reduces the sensitivity to phage DT1 when inserted in lieu of the allele of the metAP gene of *Streptococcus thermophilus* SMQ-301 strain, wherein sensitivity to phage DT1 is determined by Efficiency of Plaquing (EOP) Assay I. Thus, the LAB of the invention comprises, as the sole allele of its metAP gene, a MetAP$^R$ allele which reduces the sensitivity to phage DT1 of a *Streptococcus thermophilus* SMQ-301 derivative strain, said SMQ-301 derivative strain being a *Streptococcus thermophilus* SMQ-301 strain into which its metAP allele has been replaced by said MetAP$^R$ allele, and wherein sensitivity to phage DT1 is determined by Efficiency of Plaquing (EOP) Assay I.

In an aspect, the present invention provides a polynucleotide encoding a MetAP$^R$ protein, wherein said polynucleotide reduces the sensitivity to phage DT1 when inserted in lieu of the allele of the metAP gene of *Streptococcus thermophilus* SMQ-301 strain, wherein sensitivity to phage DT1 is determined by Efficiency of Plaquing (EOP) Assay I. Thus, the invention provides a polynucleotide encoding a MetAP$^R$ protein, wherein said polynucleotide is a metAP allele which reduces the sensitivity to phage DT1 of a *Streptococcus thermophilus* SMQ-301 derivative strain, said SMQ-301 derivative strain being a *Streptococcus thermophilus* SMQ-301 strain into which its metAP allele has been replaced by said MetAP$^R$ allele and wherein sensitivity to phage DT1 is determined by Efficiency of Plaquing (EOP) Assay I. In an embodiment, the polynucleotide consists of a MetAP$^R$ allele as defined herein. The polynucleotide comprises or consists of a MetAP$^R$ allele, as generated, as screened and/or as defined herein. The expression "reduces the sensitivity to phage DT1" is as defined herein for the definition of the MetAP$^R$ allele. In particular and as defined herein, the reduction of sensitivity to phage DT1 linked to the MetAP$^R$ allele of the invention is of at least 4 log, determined by Efficiency of Plaquing (EOP) Assay I.

Sequences of MetAP$^R$ Proteins

The MetAP$^R$ allele of the invention—as part of a polynucleotide of the invention or contained in the lactic acid bacterium of the invention—can be defined by its nucleotide sequence or by the amino acid sequence of the MetAP$^R$ protein it encodes, in addition to its ability to reduce the sensitivity to phage DT1, in particular its ability to reduce the sensitivity to phage DT1 of a *Streptococcus thermophilus* SMQ-301 derivative strain (as determined herein by the EOP Assay I).

In an embodiment, the MetAP$^R$ allele encodes a MetAP$^R$ protein comprising an amino acid suppression, an amino acid addition, an amino acid substitution or an amino acid suppression and addition, relative to a MetAP protein selected from the group consisting of:
  a) a MetAP protein having an amino acid sequence as defined in SEQ ID NO:2; and
  b) a MetAP variant protein as defined herein having at least 80% identity with SEQ ID NO:2. A MetAP variant protein as defined herein is encoded by a metAP variant allele, which when inserted in lieu of the allele of the metAP gene of *Streptococcus thermophilus* SMQ-301 strain, does not reduce the EOP or reduces the EOP of less than 3 log—wherein sensitivity to phage DT1 is determined by Efficiency of Plaquing (EOP) Assay I. A MetAP variant protein as defined herein is encoded by a metAP variant allele, which reduces the EOP of phage DT1 on a *Streptococcus thermophilus* SMQ-301 derivative strain of less than 3 log or which leads to the same EOP of phage DT1 on a *Streptococcus thermophilus* SMQ-301 derivative strain, said SMQ-301 derivative strain being a *Streptococcus thermophilus* SMQ-301 strain into which its metAP allele has been replaced by said metAP variant allele, and wherein sensitivity to phage DT1 is determined by Efficiency of Plaquing (EOP) Assay I In an embodiment, the MetAP$^R$ allele encodes a MetAP$^R$ protein the sequence of which has at least 80% identity with SEQ ID NO:2 (but is different from SEQ ID NO:2).

Particular embodiments regarding EOP, percentage of identity and size described elsewhere in this application within the context of the metAP variant protein apply similarly in the context of the MetAP$^R$ proteins.

In an embodiment, the MetAP$^R$ allele encodes a MetAP$^R$ protein comprising an amino acid suppression, relative to a MetAP protein selected from the group consisting of a) a MetAP protein having an amino acid sequence as defined in SEQ ID NO:2 and b) a MetAP variant protein as defined herein having at least 80% identity with SEQ ID NO:2; in a particular embodiment, the MetAP$^R$ protein is characterized by the suppression of at least one amino acid, in particular by the suppression of 1, 2, 3, 4 or 5 amino acids. In a particular embodiment, the MetAP$^R$ protein is characterized by the suppression of one amino acid. In a particular embodiment, the MetAP$^R$ protein is characterized by the suppression of 2, 3, 4 or 5 amino acids. In a particular embodiment, the MetAP$^R$ protein is characterized by the suppression of 2, 3, 4 or 5 consecutive amino acids.

In an embodiment, the MetAP$^R$ allele encodes a MetAP$^R$ protein comprising an amino acid addition, relative to a MetAP protein selected from the group consisting of a) a MetAP protein having an amino acid sequence as defined in SEQ ID NO:2 and b) a MetAP variant protein as defined herein having at least 80% identity with SEQ ID NO:2; in a particular embodiment, the MetAP$^R$ protein is characterized by the addition of at least one amino acid, in particular by the addition of 1, 2, 3, 4 or 5 amino acids. In a particular embodiment, the MetAP$^R$ protein is characterized by the addition of one amino acid. In a particular embodiment, the MetAP$^R$ protein is characterized by the addition of 2, 3, 4 or 5 amino acids. In a particular embodiment, the MetAP$^R$ protein is characterized by the addition of 2, 3, 4 or 5 consecutive amino acids.

In an embodiment, the MetAP$^R$ allele encodes a MetAP$^R$ protein comprising an amino acid substitution relative to a MetAP protein selected from the group consisting of a) a MetAP protein having an amino acid sequence as defined in SEQ ID NO:2 and b) a MetAP variant protein as defined herein having at least 80% identity with SEQ ID NO:2; in a particular embodiment, the MetAP$^R$ protein is characterized by the substitution of at least one amino acid, in particular by the substitution of 1, 2, 3, 4 or 5 amino acids. In a particular embodiment, the MetAP$^R$ protein is characterized by the substitution of one amino acid. In a particular embodiment, the MetAP$^R$ protein is characterized by the substitution of 2, 3, 4 or 5 amino acids.

In one embodiment, the MetAP$^R$ allele encodes a MetAP$^R$ protein, wherein the sequence of said MetAP$^R$ protein does not comprise an amino acid selected from the group consisting of a glutamine at position 57, a leucine at position 153, an alanine at position 168, a histidine at position 206, a valine at position 228 and a proline at position 233, wherein the amino acid sequence set forth in SEQ ID NO:2 is used for numbering.

In one embodiment, the MetAP$^R$ allele encodes a MetAP$^R$ protein, wherein the sequence of said MetAP$^R$ protein does not comprise a glutamine at position 57, wherein the amino acid sequence set forth in SEQ ID NO:2 is used for numbering.

In one embodiment, the MetAP$^R$ allele encodes a MetAP$^R$ protein, wherein the sequence of said MetAP$^R$ protein does not comprise a leucine at position 153, wherein the amino acid sequence set forth in SEQ ID NO:2 is used for numbering.

In one embodiment, the MetAP$^R$ allele encodes a MetAP$^R$ protein, wherein the sequence of said MetAP$^R$ protein does not comprise an alanine at position 168, wherein the amino acid sequence set forth in SEQ ID NO:2 is used for numbering.

In one embodiment, the MetAP$^R$ allele encodes a MetAP$^R$ protein, wherein the sequence of said MetAP$^R$ protein does not comprise a histidine at position 206, wherein the amino acid sequence set forth in SEQ ID NO:2 is used for numbering.

In one embodiment, the MetAP$^R$ allele encodes a MetAP$^R$ protein, wherein the sequence of said MetAP$^R$ protein does not comprise a valine at position 228, wherein the amino acid sequence set forth in SEQ ID NO:2 is used for numbering.

In one embodiment, the MetAP$^R$ allele encodes a MetAP$^R$ protein, wherein the sequence of said MetAP$^R$ protein does not comprise a proline at position 233, wherein the amino acid sequence set forth in SEQ ID NO:2 is used for numbering.

In any of these embodiments, the size of the MetAP$^R$ protein is the same as the MetAP protein as defined in SEQ ID NO:2 (286 amino acid residues).

In one embodiment, the MetAP$^R$ allele encodes a MetAP$^R$ protein comprising an amino acid selected from the group consisting of a lysine or an equivalent amino acid thereof at position 57, a proline or an equivalent amino acid thereof at position 153, a glutamic acid or an equivalent amino acid thereof at position 168, a glutamine or an equivalent amino acid thereof at position 206, an aspartic acid or an equivalent amino acid thereof at position 228, a glutamine or an equivalent amino acid thereof at position 233 and a leucine or an equivalent amino acid thereof at position 233, wherein the amino acid sequence set forth in SEQ ID NO:2 is used for numbering.

In one embodiment, the MetAP$^R$ allele encodes a MetAP$^R$ protein comprising a lysine or an equivalent amino acid thereof at position 57, wherein the amino acid sequence set forth in SEQ ID NO:2 is used for numbering.

In one embodiment, the MetAP$^R$ allele encodes a MetAP$^R$ protein comprising a proline or an equivalent amino acid thereof at position 153, wherein the amino acid sequence set forth in SEQ ID NO:2 is used for numbering.

In one embodiment, the MetAP$^R$ allele encodes a MetAP$^R$ protein comprising a glutamic acid or an equivalent amino acid thereof at position 168, wherein the amino acid sequence set forth in SEQ ID NO:2 is used for numbering.

In one embodiment, the MetAP$^R$ allele encodes a MetAP$^R$ protein comprising a glutamine or an equivalent amino acid thereof at position 206, wherein the amino acid sequence set forth in SEQ ID NO:2 is used for numbering.

In one embodiment, the MetAP$^R$ allele encodes a MetAP$^R$ protein comprising an aspartic acid or an equivalent amino acid thereof at position 228, wherein the amino acid sequence set forth in SEQ ID NO:2 is used for numbering.

In one embodiment, the MetAP$^R$ allele encodes a MetAP$^R$ protein comprising a glutamine or an equivalent amino acid thereof at position 233, wherein the amino acid sequence set forth in SEQ ID NO:2 is used for numbering.

In one embodiment, the MetAP$^R$ allele encodes a MetAP$^R$ protein comprising a leucine or an equivalent amino acid thereof at position 233, wherein the amino acid sequence set forth in SEQ ID NO:2 is used for numbering.

In any of these embodiments, the size of the MetAP$^R$ protein is the same as the MetAP protein as defined in SEQ ID NO:2 (286 amino acid residues).

In one embodiment, the MetAP$^R$ allele encodes a MetAP$^R$ protein comprising an amino acid selected from the group consisting of a lysine at position 57, a proline at position 153, a glutamic acid at position 168, a glutamine at position 206, an aspartic acid at position 228, a glutamine at position 233 and a leucine at position 233, wherein the amino acid sequence set forth in SEQ ID NO:2 is used for numbering.

In one embodiment, the MetAP$^R$ allele encodes a MetAP$^R$ protein comprising a lysine at position 57, wherein the amino acid sequence set forth in SEQ ID NO:2 is used for numbering.

In one embodiment, the MetAP$^R$ allele encodes a MetAP$^R$ protein comprising a proline at position 153, wherein the amino acid sequence set forth in SEQ ID NO:2 is used for numbering.

In one embodiment, the MetAP$^R$ allele encodes a MetAP$^R$ protein comprising a glutamic acid at position 168, wherein the amino acid sequence set forth in SEQ ID NO:2 is used for numbering.

In one embodiment, the MetAP$^R$ allele encodes a MetAP$^R$ protein comprising a glutamine at position 206, wherein the amino acid sequence set forth in SEQ ID NO:2 is used for numbering.

In one embodiment, the MetAP$^R$ allele encodes a MetAP$^R$ protein comprising an aspartic acid at position 228, wherein the amino acid sequence set forth in SEQ ID NO:2 is used for numbering.

In one embodiment, the MetAP$^R$ allele encodes a MetAP$^R$ protein comprising a glutamine at position 233, wherein the amino acid sequence set forth in SEQ ID NO:2 is used for numbering.

In one embodiment, the MetAP$^R$ allele encodes a MetAP$^R$ protein comprising a leucine at position 233, wherein the amino acid sequence set forth in SEQ ID NO:2 is used for numbering.

In any of these embodiments, the size of the MetAP$^R$ protein is the same as the MetAP protein as defined in SEQ ID NO:2 (286 amino acid residues).

In one embodiment, the MetAP$^R$ allele encodes a MetAP$^R$ protein comprising:
  a) an amino acid sequence which is otherwise as defined in SEQ ID NO:2, but which does not comprise an amino acid selected from the group consisting of a glutamine at position 57, a leucine at position 153, an alanine at position 168, a histidine at position 206, a valine at position 228 and a proline at position 233; these MetAP$^R$ alleles encode the MetAP$^R$ proteins as set forth in SEQ ID NO:5 to 10 respectively;
  b) an amino acid sequence which has 80% identity with SEQ ID NO:2 and which does not comprise an amino acid selected from the group consisting of a glutamine at position 57, a leucine at position 153, an alanine at position 168, a histidine at position 206, a valine at position 228 and a proline at position 233; or
  c) an amino acid sequence which is otherwise the one of a MetAP variant protein having at least 80% identity with SEQ ID NO:2 (MetAP variant protein as defined herein), but which does not comprise an amino acid selected from the group consisting of a glutamine at position 57, a leucine at position 153, an alanine at position 168, a histidine at position 206, a valine at position 228 and a proline at position 233.

In one embodiment, the MetAP$^R$ allele encodes a MetAP$^R$ protein comprising an amino acid sequence which is otherwise as defined in SEQ ID NO:2 but which does not comprise a glutamine at position 57 (SEQ ID NO:5), comprising an amino acid sequence which has 80% identity with SEQ ID NO:2 and which does not comprise a glutamine at position 57, or comprising an amino acid sequence which is otherwise the one of a MetAP variant protein having at least 80% identity with SEQ ID NO:2, but which does not comprise a glutamine at position 57.

In one embodiment, the MetAP$^R$ allele encodes a MetAP$^R$ protein comprising an amino acid sequence which is otherwise as defined in SEQ ID NO:2 but which does not comprise a leucine at position 153 (SEQ ID NO:6), comprising an amino acid sequence which has 80% identity with SEQ ID NO:2 and which does not comprise a leucine at position 153, or comprising an amino acid sequence which is otherwise the one of a MetAP variant protein having at least 80% identity with SEQ ID NO:2, but which does not comprise a leucine at position 153.

In one embodiment, the MetAP$^R$ allele encodes a MetAP$^R$ protein comprising an amino acid sequence which is otherwise as defined in SEQ ID NO:2, but which does not comprise an alanine at position 168 (SEQ ID NO:7), comprising an amino acid sequence which has 80% identity with SEQ ID NO:2 and which does not comprise an alanine at position 168, or comprising an amino acid sequence which is otherwise the one of a MetAP variant protein having at least 80% identity with SEQ ID NO:2, but which does not comprise an alanine at position 168.

In one embodiment, the MetAP$^R$ allele encodes a MetAP$^R$ protein comprising an amino acid sequence which is otherwise as defined in SEQ ID NO:2, but which does not comprise a histidine at position 206 (SEQ ID NO:8), comprising an amino acid sequence which has 80% identity with SEQ ID NO:2 and which does not comprise a histidine at position 206, or comprising an amino acid sequence which is otherwise the one of a MetAP variant protein having at least 80% identity with SEQ ID NO:2, but which does not comprise a histidine at position 206.

In one embodiment, the MetAP$^R$ allele encodes a MetAP$^R$ protein comprising an amino acid sequence which is otherwise as defined in SEQ ID NO:2, but which does not comprise a valine at position 228 (SEQ ID NO:9), comprising an amino acid sequence which has 80% identity with SEQ ID NO:2 and which does not comprise a valine at position 228, or comprising an amino acid sequence which is otherwise the one of a MetAP variant protein having at least 80% identity with SEQ ID NO:2, but which does not comprise a valine at position 228.

In one embodiment, the MetAP$^R$ allele encodes a MetAP$^R$ protein comprising an amino acid sequence which is otherwise as defined in SEQ ID NO:2, but which does not comprise a proline at position 233 (SEQ ID NO:10), comprising an amino acid sequence which has 80% identity with SEQ ID NO:2 and which does not comprise a proline at position 233, or comprising an amino acid sequence which is otherwise the one of a MetAP variant protein having at least 80% identity with SEQ ID NO:2, but which does not comprise a proline at position 233.

In any of these embodiments, the size of the MetAP$^R$ protein is the same as the MetAP protein as defined in SEQ ID NO:2 (286 amino acid residues).

In one embodiment, the MetAP$^R$ allele encodes a MetAP$^R$ protein comprising:
a) an amino acid sequence which is otherwise as defined in SEQ ID NO:2, but which comprises an amino acid substitution selected from the group consisting of a lysine or an equivalent amino acid thereof at position 57, a proline or an equivalent amino acid thereof at position 153, a glutamic acid or an equivalent amino acid thereof at position 168, a glutamine or an equivalent amino acid thereof at position 206, an aspartic acid or an equivalent amino acid thereof at position 228, a glutamine or an equivalent amino acid thereof at position 233 and a leucine or an equivalent amino acid thereof at position 233;
b) an amino acid sequence which has 80% identity with SEQ ID NO:2 and which comprises an amino acid residue selected from the group consisting of a lysine or an equivalent amino acid thereof at position 57, a proline or an equivalent amino acid thereof at position 153, a glutamic acid or an equivalent amino acid thereof at position 168, a glutamine or an equivalent amino acid thereof at position 206, an aspartic acid or an equivalent amino acid thereof at position 228, a glutamine or an equivalent amino acid thereof at position 233 and a leucine or an equivalent amino acid thereof at position 233; or
c) an amino acid sequence which is otherwise the one of a MetAP variant protein having at least 80% identity with SEQ ID NO:2 (MetAP variant protein as defined herein), but which comprises an amino acid substitution selected from the group consisting of a lysine or an equivalent amino acid thereof at position 57, a proline or an equivalent amino acid thereof at position 153, a glutamic acid or an equivalent amino acid thereof at position 168, a glutamine or an equivalent amino acid thereof at position 206, an aspartic acid or an equivalent amino acid thereof at position 228, a glutamine or an equivalent amino acid thereof at position 233 and a leucine or an equivalent amino acid thereof at position 233.

In one embodiment, the MetAP$^R$ allele encodes a MetAP$^R$ protein comprising an amino acid sequence which is otherwise as defined in SEQ ID NO:2 but which comprises a lysine or an equivalent amino acid thereof at position 57, comprising an amino acid sequence which has 80% identity with SEQ ID NO:2 and which comprises a lysine or an equivalent amino acid thereof at position 57, or comprising an amino acid sequence which is otherwise the one of a MetAP variant protein having at least 80% identity with SEQ ID NO:2, but which comprises a lysine or an equivalent amino acid thereof at position 57.

In one embodiment, the MetAP$^R$ allele encodes a MetAP$^R$ protein comprising an amino acid sequence which is otherwise as defined in SEQ ID NO:2 but which comprises a proline or an equivalent amino acid thereof at position 153, comprising an amino acid sequence which has 80% identity with SEQ ID NO:2 and which comprises a proline or an equivalent amino acid thereof at position 153, or comprising an amino acid sequence which is otherwise the one of a MetAP variant protein having at least 80% identity with SEQ ID NO:2, but which comprises a proline or an equivalent amino acid thereof at position 153.

In one embodiment, the MetAP$^R$ allele encodes a MetAP$^R$ protein comprising an amino acid sequence which is otherwise as defined in SEQ ID NO:2 but which comprises a glutamic acid or an equivalent amino acid thereof at position 168, comprising an amino acid sequence which has 80% identity with SEQ ID NO:2 and which comprises a glutamic acid or an equivalent amino acid thereof at position 168, or comprising an amino acid sequence which is otherwise the one of a MetAP variant protein having at least 80% identity with SEQ ID NO:2, but which comprises a glutamic acid or an equivalent amino acid thereof at position 168.

In one embodiment, the MetAP$^R$ allele encodes a MetAP$^R$ protein comprising an amino acid sequence which is otherwise as defined in SEQ ID NO:2 but which comprises a glutamine or an equivalent amino acid thereof at position 206, comprising an amino acid sequence which has 80% identity with SEQ ID NO:2 and which comprises a glutamine or an equivalent amino acid thereof at position 206, or comprising an amino acid sequence which is otherwise the one of a MetAP variant protein having at least 80% identity with SEQ ID NO:2, but which comprises a glutamine or an equivalent amino acid thereof at position 206.

In one embodiment, the MetAP$^R$ allele encodes a MetAP$^R$ protein comprising an amino acid sequence which is otherwise as defined in SEQ ID NO:2 but which comprises an aspartic acid or an equivalent amino acid thereof at position 228, comprising an amino acid sequence which has 80% identity with SEQ ID NO:2 and which comprises an aspartic acid or an equivalent amino acid thereof at position 228, or comprising an amino acid sequence which is otherwise the one of a MetAP variant protein having at least 80% identity with SEQ ID NO:2, but which comprises an aspartic acid or an equivalent amino acid thereof at position 228.

In one embodiment, the MetAP$^R$ allele encodes a MetAP$^R$ protein comprising an amino acid sequence which is otherwise as defined in SEQ ID NO:2 but which comprises a glutamine or an equivalent amino acid thereof at position 233, comprising an amino acid sequence which has 80% identity with SEQ ID NO:2 and which comprises a glutamine or an equivalent amino acid thereof at position 233, or comprising an amino acid sequence which is otherwise the one of a MetAP variant protein having at least 80% identity with SEQ ID NO:2, but which comprises a glutamine or an equivalent amino acid thereof at position 233.

In one embodiment, the MetAP$^R$ allele encodes a MetAP$^R$ protein comprising an amino acid sequence which is otherwise as defined in SEQ ID NO:2 but which comprises a leucine or an equivalent amino acid thereof at position 233, comprising an amino acid sequence which has 80% identity with SEQ ID NO:2 and which comprises a leucine or an equivalent amino acid thereof at position 233, or comprising an amino acid sequence which is otherwise the one of a MetAP variant protein having at least 80% identity with SEQ ID NO:2, but which comprises a leucine or an equivalent amino acid thereof at position 233.

In any of these embodiments, the size of the MetAP$^R$ protein is the same as the MetAP protein as defined in SEQ ID NO:2 (286 amino acid residues).

In one embodiment, the MetAP$^R$ allele encodes a MetAP$^R$ protein comprising:
a) an amino acid sequence which is otherwise as defined in SEQ ID NO:2, but which comprises an amino acid substitution selected from the group consisting of a glutamine at position 206, a lysine at position 57, a proline at position 153, a glutamic acid at position 168, an aspartic acid at position 228, a glutamine at position 233 and a leucine at position 233; these metAP$^R$ alleles encode the MetAP$^R$ proteins as set forth in SEQ ID NO:4 and 11 to 16 respectively;

b) an amino acid sequence which has 80% identity with SEQ ID NO:2 and which comprises an amino acid residue selected from the group consisting of a glutamine at position 206, a lysine at position 57, a proline at position 153, a glutamic acid at position 168, an aspartic acid at position 228, a glutamine at position 233 and a leucine at position 233; or c) an amino acid sequence which is otherwise the one of a MetAP variant protein having at least 80% identity with SEQ ID NO:2 (MetAP variant protein as defined herein), but which comprises an amino acid substitution selected from the group consisting of a lysine at position 57, a proline at position 153, a glutamic acid at position 168, a glutamine at position 206, an aspartic acid at position 228, a glutamine at position 233 and a leucine at position 233.

In one embodiment, the MetAP$^R$ allele encodes a MetAP$^R$ protein comprising an amino acid sequence which is otherwise as defined in SEQ ID NO:2 but which comprises a lysine at position 57 (SEQ ID NO:11), comprising an amino acid sequence which has 80% identity with SEQ ID NO:2 and which comprises a lysine at position 57, or comprising an amino acid sequence which is otherwise the one of a MetAP variant protein having at least 80% identity with SEQ ID NO:2, but which comprises a lysine at position 57.

In one embodiment, the MetAP$^R$ allele encodes a MetAP$^R$ protein comprising an amino acid sequence which is otherwise as defined in SEQ ID NO:2 but which comprises a proline at position 153 (SEQ ID NO:12), comprising an amino acid sequence which has 80% identity with SEQ ID NO:2 and which comprises a proline at position 153, or comprising an amino acid sequence which is otherwise the one of a MetAP variant protein having at least 80% identity with SEQ ID NO:2, but which comprises a proline at position 153.

In one embodiment, the MetAP$^R$ allele encodes a MetAP$^R$ protein comprising an amino acid sequence which is otherwise as defined in SEQ ID NO:2 but which comprises a glutamic acid at position 168 (SEQ ID NO:13), comprising an amino acid sequence which has 80% identity with SEQ ID NO:2 and which comprises a glutamic acid at position 168, or comprising an amino acid sequence which is otherwise the one of a MetAP variant protein having at least 80% identity with SEQ ID NO:2, but which comprises a glutamic acid at position 168.

In one embodiment, the MetAP$^R$ allele encodes a MetAP$^R$ protein comprising an amino acid sequence which is otherwise as defined in SEQ ID NO:2 but which comprises a glutamine at position 206 (SEQ ID NO:4), comprising an amino acid sequence which has 80% identity with SEQ ID NO:2 and which comprises a glutamine at position 206, or comprising an amino acid sequence which is otherwise the one of a MetAP variant protein having at least 80% identity with SEQ ID NO:2, but which comprises a glutamine at position 206.

In one embodiment, the MetAP$^R$ allele encodes a MetAP$^R$ protein comprising an amino acid sequence which is otherwise as defined in SEQ ID NO:2 but which comprises an aspartic acid at position 228 (SEQ ID NO:14), comprising an amino acid sequence which has 80% identity with SEQ ID NO:2 and which comprises an aspartic acid at position 228, or comprising an amino acid sequence which is otherwise the one of a MetAP variant protein having at least 80% identity with SEQ ID NO:2, but which comprises an aspartic acid at position 228.

In one embodiment, the MetAP$^R$ allele encodes a MetAP$^R$ protein comprising an amino acid sequence which is otherwise as defined in SEQ ID NO:2 but which comprises a glutamine at position 233 (SEQ ID NO:15), comprising an amino acid sequence which has 80% identity with SEQ ID NO:2 and which comprises a glutamine at position 233, or comprising an amino acid sequence which is otherwise the one of a MetAP variant protein having at least 80% identity with SEQ ID NO:2, but which comprises a glutamine at position 233.

In one embodiment, the MetAP$^R$ allele encodes a MetAP$^R$ protein comprising an amino acid sequence which is otherwise as defined in SEQ ID NO:2 but which comprises a leucine at position 233 (SEQ ID NO:16), comprising an amino acid sequence which has 80% identity with SEQ ID NO:2 and which comprises a leucine at position 233, or comprising an amino acid sequence which is otherwise the one of a MetAP variant protein having at least 80% identity with SEQ ID NO:2, but which comprises a leucine at position 233.

In any of these embodiments, the size of the MetAP$^R$ protein is the same as the MetAP protein as defined in SEQ ID NO:2 (286 amino acid residues).

In one embodiment, the MetAP$^R$ allele encodes a MetAP$^R$ protein which is obtained from a MetAP protein having a sequence as set forth in SEQ ID NO:2, by an amino acid substitution selected from the group consisting of Q57K, L153P, A168E, H206Q, V228D, P233Q and P233L. In one embodiment, the MetAP$^R$ allele encodes a MetAP$^R$ protein which is obtained from a MetAP protein variant having at least 80% identity with SEQ ID NO:2, by an amino acid substitution selected from the group consisting of Q57K, L153P, A168E, H206Q, V228D, P233Q and P233L.

In one embodiment, the MetAP$^R$ allele encodes a MetAP$^R$ protein which is obtained from a MetAP protein having a sequence as set forth in SEQ ID NO:2 or from a MetAP variant protein as defined herein having at least 80% identity with SEQ ID NO:2, by the Q57K substitution.

In one embodiment, the MetAP$^R$ allele encodes a MetAP$^R$ protein which is obtained from a MetAP protein having a sequence as set forth in SEQ ID NO:2 or from a MetAP variant protein as defined herein having at least 80% identity with SEQ ID NO:2, by the L153P substitution.

In one embodiment, the MetAP$^R$ allele encodes a MetAP$^R$ protein which is obtained from a MetAP protein having a sequence as set forth in SEQ ID NO:2 or from a MetAP variant protein as defined herein having at least 80% identity with SEQ ID NO:2, by the A168E substitution.

In one embodiment, the MetAP$^R$ allele encodes a MetAP$^R$ protein which is obtained from a MetAP protein having a sequence as set forth in SEQ ID NO:2 or from a MetAP variant protein as defined herein having at least 80% identity with SEQ ID NO:2, by the H206Q substitution.

In one embodiment, the MetAP$^R$ allele encodes a MetAP$^R$ protein which is obtained from a MetAP protein having a sequence as set forth in SEQ ID NO:2 or from a MetAP variant protein as defined herein having at least 80% identity with SEQ ID NO:2, by the V228D substitution.

In one embodiment, the MetAP$^R$ allele encodes a MetAP$^R$ protein which is obtained from a MetAP protein having a sequence as set forth in SEQ ID NO:2 or from a MetAP variant protein as defined herein having at least 80% identity with SEQ ID NO:2, by the P233Q substitution.

In one embodiment, the MetAP$^R$ allele encodes a MetAP$^R$ protein which is obtained from a MetAP protein having a sequence as set forth in SEQ ID NO:2 or from a MetAP variant protein as defined herein having at least 80% identity with SEQ ID NO:2, by the P233L substitution.

In any of these embodiments, the size of the MetAP$^R$ protein is the same as the MetAP protein as defined in SEQ ID NO:2 (286 amino acid residues).

In one embodiment, the MetAP$^R$ allele encodes a MetAP$^R$ protein comprising an amino acid sequence which is truncated in its last quarter. By "last quarter", it is meant the C terminal part of the MetAP protein comprised from the residue 215 to the residue 286, wherein the amino acid sequence set forth in SEQ ID NO:2 is used for numbering. Therefore, in an embodiment, the MetAP$^R$ allele encodes a MetAP$^R$ protein comprising a stop codon at a residue comprised from the residue 215 to the residue 286, wherein the amino acid sequence set forth in SEQ ID NO:2 is used for numbering. In an embodiment, the MetAP$^R$ allele encodes a MetAP$^R$ protein comprising a stop codon at a residue comprised from the residue 226 to the residue 286, wherein the amino acid sequence set forth in SEQ ID NO:2 is used for numbering.

In an embodiment, the MetAP$^R$ allele encodes a MetAP$^R$ protein comprising an amino acid sequence which is truncated in its last quarter, wherein the sequence of said MetAP$^R$ protein has at least 80% identity with the corresponding part of SEQ ID NO:2. By "corresponding part", it is meant that the percentage identity is calculated based on the alignment of the 2 sequences for the same amino acid range starting at residue 1 until the position of the stop codon (as an example, if the protein is truncated at position 226, the 80% identity of the MetAP$^R$ protein with SEQ ID NO:2 is calculated based on the alignment of the 2 sequences for residues 1 to 226). By "at least 80% identity with the corresponding part of SEQ ID NO:2", it is meant at least 85%, at least 90%, at least 95%, at least 96%, at least 97%, at least 98% and at least 99% with the corresponding part of SEQ ID NO:2. In an embodiment, the MetAP$^R$ allele encodes a MetAP$^R$ protein comprising an amino acid sequence which is otherwise as defined in SEQ ID NO:2 but which comprises a stop codon in its last quarter.

In an embodiment, the stop codon results from an insertion and/or deletion of nucleotide(s).

In an embodiment, the stop codon results from the substitution of one nucleotide; in an embodiment, the MetAP$^R$ allele encodes a MetAP$^R$ protein truncated at position 226 (i.e., presenting a stop codon at position 226), wherein the amino acid sequence set forth in SEQ ID NO:2 is used for numbering. In an embodiment, the codon 226 of the MetAP$^R$ allele is TGA.

In one embodiment, the MetAP$^R$ allele encodes a MetAP$^R$ protein comprising an amino acid sequence which is otherwise as defined in SEQ ID NO:2 but which comprises a stop codon at position 226 (SEQ ID NO:17), comprising an amino acid sequence which has 80% identity with SEQ ID NO:2 and which comprises a stop codon at position 226, or comprising an amino acid sequence which is otherwise the one of a MetAP variant protein having at least 80% identity with SEQ ID NO:2 (MetAP variant protein as defined herein), but which comprises a stop codon at position 226.

In one embodiment, the MetAP$^R$ allele encodes a MetAP$^R$ protein which is obtained from a MetAP protein having a sequence as set forth in SEQ ID NO:2, in which the glycine at position 226 is substituted with a stop codon. In one embodiment, the MetAP$^R$ allele encodes a MetAP$^R$ protein which is obtained from a MetAP variant protein as defined herein having at least 80% identity with SEQ ID NO:2, in which the glycine at position 226 is substituted with a stop codon.

Amino Acid Numbering

In the present invention, a specific numbering of amino acid residue positions is used for the characterization of the MetAP protein of the present invention. By alignment of the amino acid sequence of a candidate MetAP protein, of a MetAP$^R$ protein or of a MetAP variant protein, with the MetAP protein defined in SEQ ID NO:2, it is possible to allot a number to an amino acid residue position in said candidate MetAP protein, said MetAP$^R$ protein or said MetAP variant protein respectively, which corresponds with the amino acid residue position or numbering of the amino acid sequence shown in SEQ ID NO:2.

An alternative way of describing the amino acid numbering used in this application is to say that amino acid positions are identified by those 'corresponding' to a particular position in the amino acid sequence shown in SEQ ID NO:2. This is not to be interpreted as meaning the sequences of the present invention must include the amino acid sequence shown in SEQ ID NO:2. A skilled person will readily appreciate that MetAP protein sequences vary among different bacterial strains. Reference to the amino acid sequence shown in SEQ ID NO:2 is used merely to enable identification of a particular amino acid location within any particular MetAP protein. Such amino acid locations can be routinely identified using sequence alignment programs, the use of which are well known in the art.

Lactic Acid Bacteria

As used herein the term "lactic acid bacteria" or "lactic acid bacterium" or "LAB" refers to Gram positive, bacteria which ferment sugars to produce exclusively or predominantly lactic acid.

In one aspect, the present invention provides a lactic acid bacterium comprising a metAP$^R$ allele of the invention. In another aspect, the present invention provides a lactic acid bacterium comprising a polynucleotide of the invention.

The industrially most useful lactic acid bacteria are found among the genera *Streptococcus, Lactococcus, Lactobacillus, Leuconostoc, Pediococcus, Enterococcus, Oenococcus* and *Bifidobacterium*. In one embodiment, it is therefore preferred that the lactic acid bacterium is selected from this group of genera.

In an embodiment, the lactic acid bacterium of the invention is of the *Streptococcus* genus. In an embodiment, the lactic acid bacterium of the invention is of the species *Streptococcus thermophilus* or *Streptococcus mutans*. In an embodiment, the lactic acid bacterium of the invention is of the species *Streptococcus thermophilus*.

In an embodiment, the lactic acid bacterium of the invention may be engineered to comprise a MetAP$^R$ allele of the invention as described herein. As described above, "comprising a MetAP$^R$ allele" means that the sole allele of the metAP gene contained in the genome of the LAB is a MetAP$^R$ allele. In an embodiment, the lactic acid bacterium of the invention comprises, as the sole allele of its metAP gene, a MetAP$^R$ allele of the invention.

Such lactic acid bacterium may be engineered by replacing the original allele of its metAP gene by a MetAP$^R$ allele of the invention; the replacement can be done using conventional techniques as defined herein.

In another embodiment, such lactic acid bacterium may be engineered by a method comprising:
 a) challenging a parental LAB strain sensitive to a cos-type phage (reference strain) by said cos-type phage;

b) selecting the strains which have a reduced sensitivity to said cos-type phage, wherein sensitivity to said cos-type phage is determined by Efficiency of Plaquing (EOP) Assay I;

c) selecting from the strains having a reduced sensitivity to said cos-type phage identified in step b), the strains which have a metAP allele the sequence of which is different from the metAP allele of the parental LAB strain; and d) checking that the metAP allele of the strains identified in step c) is a MetAP$^R$ allele as defined herein.

A suitable protocol for the challenge of a strain by a phage of step a) is described in the materials and methods section. The reduced sensitivity (step b) is determined by Efficiency of Plaquing (EOP) Assay I as defined herein using the parental LAB strain as a reference strain. In a particular embodiment, the reduced sensitivity is characterized by a EOP reduction of at least 4 log, at least 5 log, at least 6 log, at least 7 log or at least 8 log, when determined by the EOP Assay I. The difference of sequence between the metAP gene of the strains identified in step b) and the metAP gene of the parental strain can be carried out by any conventional methods, such as DNA sequencing. In a particular embodiment, the checking step d) is carried out using a method to identify a MetAP$^R$ allele encoding a MetAP$^R$ protein as defined herein.

In an embodiment, the method also comprises an additional step [step b1], between step b) and step c), consisting in comparing the CRISPR locus or loci of the strains identified in step b) and of the parental LAB strain, and selecting the strains the CRISPR locus or loci of which has (have) not been modified as compared to the corresponding CRISPR locus or loci of the parental LAB strain. The CRISPR locus comparison can be carried out by comparing the length of the CRISPR locus or loci, or by sequencing the CRISPR locus or loci. Step c) is then carried out on the strains selected by step b1).

Bacteriophage

As used herein, the term "bacteriophage" has its conventional meaning as understood in the art, i.e., a virus that selectively infects bacteria. Many bacteriophages are specific to a particular genus or species or strain of bacteria. The term "bacteriophage" is synonymous with the term "phage".

The definition of "cos-type phages" is according to the art and referred to the presence of a specific sequence (cos site) needed for the packaging of the phage DNA. Thus, cos-type phages incorporate cohesive "sticky" ends into their genomes (cos site), in contrast to pac-type phages which employ a so-called headful DNA packaging system and, therefore, may incorporate additional redundant DNA into their genomes (pac site), cos-type phages that infect species of bacteria, including lactic acid bacteria, are known and can be identified based on their DNA packaging strategy or on genetic or genomic analyses.

In *S. thermophilus*, cos- and pac-type phages (Siphoviridae family) are detailed in Le Marrec et al. (1997). A representative cos-type phage infecting *Streptococcus thermophilus* strains is the phage DT1 (described herein).

A representative cos-type phage infecting *Streptococcus mutans* strains is the phage M102AD, which is described in Delisle et al. (2012). The M102AD phage is available at the Félix d'Hérelle Reference Centre for Bacterial Viruses, under reference HER503. The host strain of this phage is *Streptococcus mutans* HER 1503 which is available at Félix d'Hérelle Reference Centre for Bacterial Viruses, under reference HER1503.

Polynucleotide

In a further aspect, the present invention provides a polynucleotide comprising or consisting of a MetAP$^R$ allele [encoding a MetAP$^R$ protein] of the invention. In one embodiment, the polynucleotide is a MetAP$^R$ allele [encoding a MetAP$^R$ protein] of the invention.

In an embodiment, the size of the polynucleotide of the invention is at least 843 nucleotides, at least 846 nucleotides, at least 849 nucleotides, at least 852 nucleotides, at least 855 nucleotides, at least 858 nucleotides or at least 861 nucleotides. In an embodiment, the size of the polynucleotide of the invention is less than 3 kb, less than 2 kb or less than 1 kb. In an embodiment, the size of the polynucleotide ranges from a minimal size selected from the group consisting of at least 843 nucleotides, at least 846 nucleotides, at least 849 nucleotides, at least 852 nucleotides, at least 855 nucleotides, at least 858 nucleotides and at least 861 nucleotides to a maximal size selected from the group consisting of 1 kb, 2 kb and 3 kb. In an embodiment, the size of the polynucleotide is 858 or 861 nucleotides.

In an embodiment, the polynucleotide of the invention consists of a MetAP$^R$ allele as defined herein, independently flanked on one side (in 5' and in 3') or on both sides of a nucleotide region ranging from 500 bp to 1 kb.

Typically, the polynucleotide encompassed by the scope of the present invention is prepared using recombinant DNA techniques (i.e. recombinant DNA), as described herein. However, in an alternative embodiment of the invention, the polynucleotide could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

A polynucleotide encoding a MetAP$^R$ protein as defined herein may be identified and/or isolated and/or purified from any lactic acid bacterium. Various methods are well known within the art for the identification and/or isolation and/or purification of polynucleotides.

By way of example, PCR amplification techniques to prepare more copies of a polynucleotide may be used once a suitable polynucleotide has been identified and/or isolated and/or purified.

By way of further example, a genomic DNA library may be constructed using chromosomal DNA from the lactic acid bacteria producing the MetAP$^R$ protein. Based on the sequence of the MetAP$^R$ protein, oligonucleotide probes may be synthesised and used to identify protein-encoding clones from the genomic library prepared from the lactic acid bacteria.

Alternatively, the polynucleotide encoding the MetAP$^R$ protein of the invention may be prepared synthetically by established standard methods, e.g. the phosphoroamidite method described by Beucage S. L. et al., 1981, *Tetrahedron Letters* 22:1859-1869, or the method described by Matthes et al., 1984, EMBO J., 3:801-805. In the phosphoroamidite method, oligonucleotides are synthesised, e.g. in an automatic DNA synthesiser, purified, annealed, ligated and cloned in appropriate vectors.

The polynucleotide may be prepared by polymerase chain reaction (PCR) using specific primers, for instance as described in U.S. Pat. No. 4,683,202 or in Saiki R K et al., 1988, *Science*, 239:487-491.

The polynucleotide and the nucleic acids encompassed by the present invention may be isolated or substantially purified. By "isolated" or "substantially purified" is intended that the polynucleotides are substantially or essentially free from components normally found in association with the polynucleotide in its natural state. Such components include other cellular material, culture media from recombinant production, and various chemicals used in chemically synthesising the nucleic acids.

An "isolated" polynucleotide or nucleic acid is typically free of nucleic acid sequences that flank the nucleic acid of interest in the genomic DNA of the organism from which the nucleic acid was derived (such as coding sequences present at the 5' or 3' ends). However, the molecule may include some additional bases or moieties that do not deleteriously affect the basic characteristics of the composition.

Vector

The invention is also directed to a vector comprising the polynucleotide of the invention. In an embodiment, this vector is a plasmid.

In an embodiment, the vector contains one or more selectable marker genes, such as a gene which confers antibiotic resistance e.g. ampicillin, kanamycin, chloramphenicol or tetracycline resistance. In an embodiment, the vector comprises a nucleotide sequence enabling the vector to replicate in the host cell in question. Examples of such sequences are the origins of replication of plasmids pUC19, pACYC177, pUBI 10, pE194, pAMBI and pIJ702.

A vector of the invention can be used to engineer a lactic acid bacterium of the invention.

Use and Methods Based on the Polynucleotide or Vector of the Invention

In an embodiment, the invention is directed to the use of a polynucleotide or vector of the invention to reduce the sensitivity to at least one cos-type phage of a lactic acid bacterium sensitive to cos-type phages. It is not contemplated that the LAB of the invention comprises several alleles of the metAP gene. Thus, the polynucleotide or vector is used such that the resulting lactic acid bacterium comprises in its genome one MetAP$^R$ allele of the metAP gene. In an embodiment, the polynucleotide or vector is used such that the allele of the metAP gene of the original lactic acid bacterium is replaced by the polynucleotide of the invention; the replacement can be done using conventional techniques as defined herein.

In an aspect, the invention is directed to a method to prepare a lactic acid bacteria strain having a reduced sensitivity to at least one cos-type phage, comprising:
a) providing a lactic acid bacteria strain sensitive to cos-type phages (reference strain);
b) replacing the metAP gene of said lactic acid bacteria strain sensitive to cos-type phages with a polynucleotide of the invention; and
c) recovering the lactic acid bacteria strain(s) having reduced sensitivity to at least one cos-type phage.

In an embodiment, step b) consists in replacing the metAP gene of said lactic acid bacteria strain sensitive to cos-type phages with a polynucleotide consisting of a metAP$^R$ allele of the invention.

In an aspect, the invention is directed to a method to prepare a lactic acid bacteria strain having a reduced sensitivity to at least one cos-type phage, comprising:
a) providing a lactic acid bacteria strain sensitive to cos-type phages (reference strain);
b) modifying the metAP gene of a lactic acid bacteria strain sensitive to cos-type phages to have the same sequence as a MetAP$^R$ allele of the invention; and
c) recovering the lactic acid bacteria strain(s) having reduced sensitivity to at least one cos-type phage.

In an embodiment of these 2 methods, the lactic acid bacterium is of the *Streptococcus* genus. In an embodiment, the lactic acid bacterium is of the species *Streptococcus thermophilus* or *Streptococcus mutans*. In an embodiment, the lactic acid bacterium is of the species *Streptococcus thermophilus*.

Within the use or methods of the invention, the sensitivity of the lactic acid bacterium to the bacteriophage can be determined by calculating the efficiency of plaquing (EOP) in the Efficiency of Plaquing Assay I described herein.

By "reduction of the sensitivity to cos-type phages", it is meant a EOP reduction of at least 4 log, when determined by EOP Assay I. In an embodiment, the EOP reduction is of at least 5 log. In an embodiment, the EOP reduction is of at least 6 log. In an embodiment, the EOP reduction is of at least 7 log. In an embodiment, the EOP reduction is of at least 8 log.

Lactic Acid Bacteria Comprising a Polynucleotide of the Invention

The invention is directed to a lactic acid bacterium comprising a polynucleotide of the invention.

In a further aspect, the invention is directed to a lactic acid bacterium obtained by the use or the method of the invention.

In a yet further aspect, the invention provides a lactic acid bacterium according to the invention produced by the method of the invention.

The definition given above under the section "lactic acid bacteria" applies similarly herein.

In an embodiment, the lactic acid bacterium is of the *Streptococcus* genus. In an embodiment, the lactic acid bacterium is of the species *Streptococcus thermophilus* or *Streptococcus mutans*. In an embodiment, the lactic acid bacterium is of the species *Streptococcus thermophilus*.

In an embodiment, the lactic acid bacterium of the invention may be engineered to comprise a polynucleotide of the invention. It is not contemplated that the LAB of the invention comprises several alleles of the metAP gene. In an embodiment, the lactic acid bacterium of the invention comprises, as the sole allele of its metAP gene, a polynucleotide of the invention. Such lactic acid bacteria may be engineered by replacing the original allele of its metAP gene by a polynucleotide of the invention; the replacement can be done using conventional techniques as defined herein. In an embodiment, the lactic acid bacterium of the invention is engineered by a method to prepare a strain of lactic acid bacterium as described herein.

Bacterial Composition

The invention is also directed to a bacterial composition comprising or consisting of at least one, preferably one, lactic acid bacteria strain of the invention. In a particular embodiment, the lactic acid bacterium is *Streptococcus thermophilus*. In one embodiment, the bacterial composition is a pure culture, i.e., comprises or consists of a single lactic acid bacterium strain of the invention. In another embodiment, the bacterial composition is a mixed culture, i.e. comprises or consists of the lactic acid bacteria strain(s) of the invention and at least one other bacterial strain. In one embodiment, the bacterial composition is a pure culture, i.e., comprises or consists of a single *Streptococcus thermophilus* strain of the invention. In another embodiment, the bacterial composition is a mixed culture, i.e. comprises or consists of the *Streptococcus thermophilus* strain(s) of the invention and at least one other bacterial strain. By "at least" one other bacteria strain, it is meant 1 or more, and in particular 1, 2, 3, 4 or 5 strains.

Thus, in one embodiment, a bacterial composition of the invention comprises or consists of the lactic acid bacteria strain(s) of the invention, such as *Streptococcus thermophilus* strain(s), and one or more further lactic acid bacterium of the species selected from the group consisting of a *Lactococcus* species, a *Streptococcus* species, a *Lactobacillus* species including *Lactobacillus acidophilus*, an *Enterococcus* species, a *Pediococcus* species, a *Leuconostoc* species, a *Bifidobacterium* species and an *Oenococcus* species or any combination thereof. *Lactococcus* species include *Lactococcus lactis*, including *Lactococcus lactis* subsp. *lactis*, *Lactococcus lactis* subsp. *cremoris* and *Lactococcus lactis* subsp. *lactis* biovar diacetylactis. *Bifidobacterium* species includes *Bifidobacterium animalis*, in particular *Bifidobacterium animalis* subsp *lactis*. Other lactic acid bacteria species include *Leuconostoc* sp., *Streptococcus thermophilus*, *Lactobacillus delbrueckii* subsp. *bulgaricus*, and *Lactobacillus helveticus*.

In one embodiment, the bacterial composition comprises or consists of *Streptococcus thermophilus* strain(s) of the invention, and at least one *Streptococcus thermophilus* strain, different from the *Streptococcus thermophilus* strain(s) of the invention and/or at least one strain of the *Lactobacillus* species, and/or any combination thereof. In a particular embodiment, the bacterial composition comprises or consists of the *Streptococcus thermophilus* strain(s) of the invention, one or several strain(s) of the species *Lactobacillus delbrueckii* subsp. *bulgaricus* and/or one or several strain(s) of the species *Lactobacillus helveticus* and/or any combination thereof, and optionally at least one *Streptococcus thermophilus* strain, different from the *Streptococcus thermophilus* strain(s) of the invention. In a particular embodiment, the bacterial composition comprises or consists of the *Streptococcus thermophilus* strain(s) of the invention, at least one strain of species *Streptococcus thermophilus*, different from the *Streptococcus thermophilus* strain(s) of the invention, and a strain of the species *Lactobacillus delbrueckii* subsp. *bulgaricus*. In another particular embodiment, the bacterial composition comprises or consists of the *Streptococcus thermophilus* strain(s) of the invention, and a strain of the species *Lactobacillus delbrueckii* subsp. *bulgaricus*.

In one embodiment, the bacterial composition comprises or consists of the lactic acid bacteria strain(s) of the invention, a *Lactococcus lactis* subsp. *lactis* and/or a *Lactococcus lactis* subsp. *cremoris*. In one embodiment, the bacterial composition comprises or consists of the *Streptococcus thermophilus* strain(s) of the invention, a *Lactococcus lactis* subsp. *lactis* and/or a *Lactococcus lactis* subsp. *cremoris*.

In a particular embodiment of any bacterial composition defined herein, either as a pure or mixed culture, the bacterial composition further comprises at least one probiotic strain such as *Bifidobacterium animalis* subsp. *lactis*, *Lactobacillus acidophilus*, *Lactobacillus paracasei*, or *Lactobacillus casei*.

In a particular embodiment, the bacterial composition, either as a pure or mixed culture as defined above is in frozen, dried, freeze-dried, liquid or solid format, in the form of pellets or frozen pellets, or in a powder or dried powder. In a particular embodiment, the bacterial composition of the invention is in a frozen format or in the form of pellets or frozen pellets, in particular contained into one or more boxes or sachets. In another embodiment, the bacterial composition as defined herein is in a powder form, such as a dried or freeze-dried powder, in particular contained into one or more boxes or sachets.

In a particular embodiment, the bacterial composition of the invention, either as a pure culture or mixed culture as defined above, and whatever the format (frozen, dried, freeze-dried, liquid or solid format, in the form of pellets or frozen pellets, or in a powder or dried powder) comprises the lactic acid bacteria strain(s) of the invention in a concentration comprised in the range of $10^5$ to $10^{12}$ cfu (colony forming units) per gram (cfu/g) of the bacterial composition. In a particular embodiment, the concentration of the lactic acid bacteria strain(s) within the bacterial composition of the invention is in the range of $10^7$ to $10^{12}$ cfu per gram of the bacterial composition, and in particular at least $10^7$, at least $10^8$, at least $10^9$, at least $10^{10}$ or at least $10^{11}$ cfu/g of the bacterial composition. In a particular embodiment, when in the form of frozen or dried concentrate, the concentration of the lactic acid bacteria strain(s) of the invention—as pure culture or as a mixed culture—within the bacterial composition is in the range of $10^8$ to $10^{12}$ cfu/g of frozen concentrate or dried concentrate, and more preferably at least $10^8$, at least $10^9$, at least $10^{10}$, at least $10^{11}$ or at least $10^{12}$ cfu/g of frozen concentrate or dried concentrate.

In a particular embodiment, the bacterial composition of the invention, either as a pure culture or mixed culture as defined above, and whatever the format (frozen, dried, freeze-dried, liquid or solid format, in the form of pellets or frozen pellets, or in a powder or dried powder) comprises the *Streptococcus thermophilus* strain(s) of the invention in a concentration comprised in the range of $10^5$ to $10^{12}$ cfu (colony forming units) per gram of the bacterial composition. In a particular embodiment, the concentration of the *Streptococcus thermophilus* strain(s) within the bacterial composition of the invention is in the range of $10^7$ to $10^{12}$ cfu per gram of the bacterial composition, and in particular at least $10^7$, at least $10^8$, at least $10^9$, at least $10^{10}$ or at least $10^{11}$ cfu/g of the bacterial composition. In a particular embodiment, when in the form of frozen or dried concentrate, the concentration of *Streptococcus thermophilus* strain(s)—as pure culture or as a mixed culture—within the bacterial composition is in the range of $10^8$ to $10^{12}$ cfu/g of frozen concentrate or dried concentrate, and more preferably at least $10^8$, at least $10^9$, at least $10^{10}$, at least $10^{11}$ or at least $10^{12}$ cfu/g of frozen concentrate or dried concentrate.

In an embodiment, whatever the number and nature of strains, the format of the composition and the concentration of the strain(s), the bacterial composition further comprises a food acceptable component.

In a further aspect, there is provided a method for manufacturing a fermented product comprising a) inoculating a substrate with the lactic acid bacterium or bacterial composition according to the invention and b) fermenting the inoculated substrate to obtain a fermented product. In a particular embodiment, the lactic acid bacteria strain(s) of the invention is inoculated as a bacterial composition as defined herein, such as a pure culture or a mixed culture. Preferably, the substrate is a milk substrate, more preferably milk. By "milk substrate", it is meant milk of animal and/or plant origin. In a particular embodiment, the milk substrate is of animal origin, in particular of any mammals, such as cow, goat, sheep, buffalo, zebra, horse, donkey, or camel, and the like. The milk may be in the native state, a reconstituted milk, a skimmed milk, or a milk supplemented with compounds necessary for the growth of the bacteria or for the subsequent processing of fermented milk. Preferably, the milk substrate comprises solid items. Preferably, the solid items comprise or consist of fruits, chocolate products, or cereals. Preferably, the fermented product is a fermented dairy product. Therefore, in a particular embodiment, the invention also provides a method for manufacturing a fermented dairy product, comprising a) inoculating a milk substrate with the *Streptococcus thermophilus* strain(s) or bacterial composition of the invention and b) fermenting said inoculated milk substrate, to obtain a fermented dairy product.

The present invention also provides in a further aspect the use of the lactic acid bacterium or bacterial composition according to the present invention to manufacture a food or feed product, preferably a fermented dairy product.

The invention is also directed to a fermented dairy product, which is obtained using the lactic acid bacteria strain(s) or bacterial composition of the invention, in particular obtained or obtainable by the method of the invention. Thus, the invention is directed to a fermented dairy product comprising the lactic acid bacteria strain(s) of the invention. Preferably, the fermented dairy product comprises the *Streptococcus thermophilus* strain(s) of the invention. In a particular embodiment, the fermented dairy food product of the invention is fresh fermented milk.

Product

Any product, which is prepared from, contains or comprises a lactic acid bacterium or bacterial composition of the invention is contemplated in accordance with the present invention.

Suitable products include, but are not limited to a food or a feed product.

These include, but are not limited to, fruits, legumes, fodder crops and vegetables including derived products, grain and grain-derived products, dairy foods and dairy food-derived products, meat, poultry and seafood. Preferably, the food or feed product is a dairy, meat or cereal product.

The term "food" is used in a broad sense and includes feeds, foodstuffs, food ingredients, food supplements, and functional foods. Here, the term "food" is used in a broad sense—and covers food for humans as well as food for animals (i.e. a feed). In a preferred aspect, the food is for human consumption.

As used herein the term "food ingredient" includes a formulation, which is or can be added to foods and includes formulations which can be used at low levels in a wide variety of products that require, for example, acidification or emulsification.

As used herein, the term "functional food" means a food which is capable of providing not only a nutritional effect and/or a taste satisfaction, but is also capable of delivering a further beneficial effect to consumers. Although there is no legal definition of a functional food, most of the parties with an interest in this area agree that there are foods marketed as having specific health effects.

The lactic acid bacterium of the present invention may be—or may be added to—a food ingredient, a food supplement, or a functional food.

The food may be in the form of a solution or as a solid—depending on the use and/or the mode of application and/or the mode of administration.

The lactic acid bacterium of the present invention can be used in the preparation of food products such as confectionery products, dairy products, meat products, poultry products, fish products or bakery products.

By way of example, the bacterium can be used as an ingredient to prepare soft drinks, a fruit juice or a beverage comprising whey protein, teas, cocoa drinks, milk drinks and lactic acid bacteria drinks, yoghurt, drinking yoghurt and wine.

Preferably a food as described herein is a dairy product. More preferably, a dairy product as described herein is one or more of the following: a yoghurt, a cheese (such as an acid curd cheese, a hard cheese, a semi-hard cheese, a cottage cheese), a buttermilk, a quark, a sour cream, kefir, a fermented whey-based beverage, a koumiss, a milk beverage, a yoghurt drink, a fermented milk, a matured cream, a cheese, a fromage frais, a milk, a dairy product retentate, a process cheese, a cream dessert, or an infant milk.

Preferably, a food as described herein is a fermented food product. More preferably, a food as described herein is a fermented dairy product—such as a fermented milk, a yoghurt, a cream, a matured cream, a cheese, a fromage frais, a milk beverage, a processed cheese, a cream dessert, a cottage cheese, a yoghurt drink, a dairy product retentate, or an infant milk.

Preferably the dairy product according to the invention comprises milk of animal and/or plant origin.

Milk is understood to mean that of animal origin, in particular of any mammals such as cow, goat, sheep, buffalo, zebra, horse, donkey, or camel, and the like. The term milk also applies to what is commonly called vegetable milk, that is to say extracts of plant material which have been treated or otherwise, such as leguminous plants (soya bean, chick pea, lentil and the like) or oilseeds (colza, soya bean, sesame, cotton and the like), which extract contains proteins in solution or in colloidal suspension, which are coagulable by chemical action, by acid fermentation and/or by heat. Finally, the word milk also denotes mixtures of animal milks and of vegetable milks.

In one embodiment, the term "milk" means commercial UHT milk supplemented with 3 (w/w) of semi-skimmed milk powder pasteurized by heating during 10 min+/−1 min. at 90° C.+/−0.2° C.

Amino Acid Equivalents in the Sequence of the MetAP$^R$ Proteins of the Invention In an embodiment, the MetAP$^R$ proteins of the invention are characterized by comprising an amino acid selected from the group consisting of a lysine or an equivalent amino acid thereof at position 57, a proline or an equivalent amino acid thereof at position 153, a glutamic acid or an equivalent amino acid thereof at position 168, a glutamine or an equivalent amino acid thereof at position 206, an aspartic acid or an equivalent amino acid thereof at position 228, a glutamine or an equivalent amino acid thereof at position 233 and a leucine or an equivalent amino acid thereof at position 233.

By "equivalent amino acid thereof", it is meant any amino acid having similarity in polarity, charge, solubility, hydrophobicity, hydrophilicity, and/or the amphipathic nature of the residues, as long as the MetAP$^R$ allele encoding this MetAP$^R$ protein, reduces the sensitivity to phage DT1 (as defined herein), when inserted in lieu of the allele of the metAP gene of *Streptococcus thermophilus* SMQ-301 strain, wherein sensitivity to phage DT1 is determined by Efficiency of Plaquing (EOP) Assay I.

In an embodiment, an amino acid equivalent to lysine is selected from the group consisting of glutamic acid, aspartic acid and arginine.

In an embodiment, an amino acid equivalent to proline is selected from the group consisting of alanine and glycine.

In an embodiment, an amino acid equivalent to glutamic acid is selected from the group consisting of aspartic acid and lysine.

In an embodiment, an amino acid equivalent to glutamine is selected from the group consisting of asparagine and serine.

In an embodiment, an amino acid equivalent to aspartic acid is selected from the group consisting of glutamic acid and lysine.

In an embodiment, an amino acid equivalent to a leucine is selected from the group consisting of methionine, valine, isoleucine and phenylalanine.

Percentage of identity of the MetAP protein metAP alleles, which 1) encode a MetAP protein the sequence of which has at least 80% identity with SEQ ID NO:2, and 2) do not reduce the EOP or reduce the EOP of less than 3 log—wherein sensitivity to phage DT1 is determined by Efficiency of Plaquing (EOP) Assay I, are defined herein as metAP variant alleles (encoding MetAP variant proteins). A percentage of identity of at least 80% to SEQ ID NO:2 means a percentage of identity selected from the group consisting of at least 80%, at least 85%, at least 90%, at least 95%, at least 96%, at least 97%, at least 98% and at least 99%. In an embodiment, though the sequence of the MetAP variant protein is different from SEQ ID NO:2, the size of the MetAP variant protein is the same as the MetAP protein as defined in SEQ ID NO:2 (286 amino acid residues).

metAP alleles, which 1) encode a MetAP protein the sequence of which has at least 80% identity with SEQ ID NO:2, and 2) reduces the sensitivity to phage DT1 of a *Streptococcus thermophilus* SMQ-301 derivative strain of at least 4 log [said SMQ-301 derivative strain being a *Streptococcus thermophilus* SMQ-301 strain into which its metAP allele has been replaced by a metAP allele], wherein sensitivity to phage DT1 is determined by Efficiency of Plaquing (EOP) Assay I, are defined herein as MetAP$^R$ alleles (encoding MetAP$^R$ proteins). A percentage of identity of at least 80% to SEQ ID NO:2 means a percentage of identity selected from the group consisting of at least 80%, at least 85%, at least 90%, at least 95%, at least 96%, at least 97%, at least 98% and at least 99%. In an embodiment, though the sequence of the MetAP$^R$ protein is different from SEQ ID NO:2, the size of the MetAP$^R$ protein is the same as the MetAP protein as defined in SEQ ID NO:2 (286 amino acid residues).

Comparisons of sequences can be conducted by eye, or more usually, with the aid of readily available sequence comparison programs. These commercially or freely available computer programs can calculate similarity or identity values between two or more sequences.

A percentage of identity may be calculated over aligned, contiguous sequences, i.e. one sequence is aligned with regards to another sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the downstream amino acid residues to be put out of alignment, thus potentially resulting in a large reduction of the identity when a global alignment is performed. Consequently, most sequence comparison methods are designed to produce optimal alignments that take into consideration possible insertions and deletions without penalising unduly the overall identity score. This is achieved by inserting "gaps" in the sequence alignment to try to maximise local identity. These more complex methods assign "gap penalties" to each gap that occurs in the alignment so that, for the same number of identical amino acids, a sequence alignment with as few gaps as possible—reflecting higher relatedness between the two compared sequences— will achieve a higher score than one with many gaps. "Affine gap costs" are typically used that charge a relatively high cost for the existence of a gap and a smaller penalty for each subsequent residue in the gap (gap extension penalty). This is the most commonly used gap scoring system. High gap penalties will of course produce optimised alignments with fewer gaps. Most alignment programs allow the gap penalties to be modified. However, it is possible to use the default values when using such software for sequence comparisons, because these default values have been adjusted to provide relevant results in most cases. Calculation of the maximum percentage of identity therefore firstly requires the production of an optimal alignment, taking into consideration gap penalties. A suitable computer program for carrying out such an alignment is Vector NTI (Invitrogen Corp.). An example of software that can perform sequence comparisons includes, but is not limited to, the BLAST package (see Ausubel et al., 1999, *Short Protocols in Molecular Biology*, 4th Ed—Chapter 18).

Although the alignment quality can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom comparison table if supplied (see user manual for further details). Alternatively, percentage of similarity may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate a percentage of sequence similarity, preferably a percentage of sequence identity. The software typically does this as part of the sequence comparison and generates a numerical result.

In an embodiment, the degree of identity with regards to a protein (amino acid) sequence is determined over at least 50 contiguous amino acids, at least 100 contiguous amino acids, at least 150 contiguous amino acids, at least 200 contiguous amino acids or at least 250 contiguous amino acids.

In an embodiment, the degree of identity with regards to an amino acid or protein sequence may be determined over the whole sequence of SEQ ID NO:2.

In an embodiment, the sequences [a candidate sequence of a MetAP$^R$ variant protein and SEQ ID NO:2] are aligned by a global alignment program and the sequence identity is calculated by identifying the number of exact matches identified by the program divided by the length of the candidate sequence.

In an embodiment, the degree of sequence identity between a candidate sequence of a MetAP$^R$ variant protein and SEQ ID NO:2 is determined by: 1) aligning the two sequences by any suitable alignment program using the default scoring matrix and default gap penalties, 2) identifying the number of exact matches, where an exact match is where the alignment program has identified an identical amino acid in the two aligned sequences on a given position in the alignment and 3) dividing the number of exact matches with the length of the candidate sequence.

In an embodiment, the global alignment program is selected from the group consisting of CLUSTAL and BLAST, in particular CLUSTAL, using the default parameters, and the sequence identity is calculated by identifying the number of exact matched identified by the program divided by the length of the subject sequence. parameters, and the sequence identity is determined with the BioEdit software In an embodiment, the global alignment program is CLUSTAL using the default (www.mbio.ncsu.edu/BioEdit/bioedit.html) [selecting the "Sequence" drop-down menu, then selecting the "Pairwise alignment" sub-menu, then selecting the "Calculate identity/similarity for two sequences" menu item].

General recombinant DNA methodology techniques

The present invention employs, unless otherwise indicated, conventional techniques of biochemistry, molecular biology, microbiology and recombinant DNA, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N. Y.); B. Roe, J. Crabtree, and A. Kahn, 1996, DNA Isolation and Sequencing: *Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA Methods in Enzymology*, Academic Press. Each of these general texts is herein incorporated by reference.

The invention will now be further described by way of Examples, which are meant to serve to assist one of ordinary skill in the art in carrying out the invention and are not intended in any way to limit the scope of the invention.

EXAMPLES

Materials and Methods

Bacterial Growth and Phage Propagation

Bacterial strains, phages and plasmids are listed in Table 1. *S. thermophilus* was grown at 37° C. or 42° C. in M17 medium (Oxoid, Nepean) supplemented with 0.5% lactose (LM17). When needed, chloramphenicol (Sigma, Oakville) was added to a final concentration of 5 µg/mL for growth and selection of *S. thermophilus* strains containing pNZ123 (De Vos et al. 1987) and derivatives. Agar (LabMat, Quebec) was added to a final concentration of 1% for solid medium. *Escherichia coli* was grown with agitation at 37° C. in Luria Broth (LB) supplemented with 30 µg/mL kanamycin and 20 µg/mL chloramphenicol for selection. *Streptococcus mutans* HER1503 was grown at 37° C. and 5% $CO_2$ in Brain Heart Infusion (BHI, Difco), supplemented with 10 µg/mL of chloramphenicol when selecting for pNZ123+ cells. Phages were propagated as previously described (Hynes et al., 2017).

Bacteriophage-insensitive mutant isolation

Bacteriophage insensitive mutants (BIMs) were isolated using the soft agar overlay assay as previously described (Hynes et al., 2017). Briefly, the wild-type host *S. thermophilus* SMQ-301 was challenged with the phage DT1. The bacterial host was grown in LM17 at 42° C. until the optical density at 600 nm ($OD_{600\ nm}$) reached 0.6. Then, 300 µL of the culture was added to 3 mL of molten LM17 soft agar supplemented with calcium chloride (10 mM) and phage DT1 was added to achieve a multiplicity of infection (MOI) of 0.1. Plates were incubated at 42° C. for 16 h. The resulting colonies were streaked on LM17+1% agar and screened for spacer acquisition in CR1 and CR3 loci using primers CR1-fwd and CR1-revLong for the CR1 locus and primers CR3-fwd and CR3-rev for the CR3 locus (Hynes et al., 2017). When spacer acquisition was not detected in CRISPR arrays, BIMs were conserved for genome sequencing.

TABLE 1

Plasmids, bacterial strains and phages used in the examples.

| Plasmids | |
|---|---|
| pNZ123 | *E. coli, L. lactis* and *S. thermophilus* shuttle vector |
| pNZ123:metAP | pNZ123 with the metAP gene as set forth in SEQ ID NO: 1, cloned in XbaI site |
| pNZ123:MetAP$^{H206Q}$ | pNZ123 with metAP$^{H206Q}$ gene (SEQ ID NO: 3) cloned in XbaI site |
| pNZ123:MetAPSmut | pNZ123 with the metAP gene of *S. mutans* HER 1503, cloned in XbaI site |
| Bacterial strains | |
| *S. thermophilus* SMQ-301[1] | Host strain of cos-type phages DT1 and MD2; |
| *S. thermophilus* SMQ-1039 | *S. thermophilus* SMQ-301:MetAP$^{H206Q}$ |
| *S. thermophilus* SMQ-1040 | *S. thermophilus* SMQ-1039 + pNZ123:metAP |
| *S. thermophilus* DGCC7710 | Host strain of pac-phages 858, 2972, D3288, 4259, D4752, D4754 and D939 and cos-type phages D5691, D5913, D6037, D6215 |
| *S. thermophilus* SMQ-1041 | *S. thermophilus* DGCC7710 + pNZ123:metAP |
| *S. thermophilus* SMQ-1042 | *S. thermophilus* SMQ-1041 + pNZ123:metAP |
| *S. thermophilus* DGCC7796 | Host strain of cos-type phages D4090, D5821, D4807 and of pac-type phages D2765, D4274, D5787, D5876 |
| *S. thermophilus* SMQ-1041 | *S. thermophilus* DGCC7796:MetAP$^{H206Q}$ |
| *S. thermophilus* SMQ-1042 | *S. thermophilus* SMQ-1041 + pNZ123:metAP |
| *S. thermophilus* DGCC782 | Host strain of cos-type phages N1032, N1117, N1119, N1169, N1358, N3782 |
| *S. thermophilus* SMQ-1043 | *S. thermophilus* DGCC782:MetAP$^{H206Q}$ |
| *S. thermophilus* SMQ-1044 | *S. thermophilus* SMQ-1043 + pNZ123:metAP |
| *S. mutans* HER 1503 | Host strain of cos-type phage M102AD (metAP allele as defined in SEQ ID NO: 18) |
| *S. mutans* HER 1503 map_mut | *S. mutans* HER 1503:MetAP$^{H206Q}$ (metAP allele as defined in SEQ ID NO: 20) |
| *S. mutans* HER 1503 mm + m | *S. mutans* HER 1503 map_mut + pNZ123:MetAPSmut |
| *S. thermophilus* phages cos-type phages | |
| DT1[1], MD2 | Host *S. thermophilus* SMQ-301; |
| D2765, D4274, D5787 M5876, D5691, D5913, D6037, D6215 | Host *S. thermophilus* DGCC7796 Host *S. thermophilus* DGCC7710 |
| N1032, N1117, N1119, N1169, N1358, N3782 | Host *S. thermophilus* DGCC782 |
| pac-type phages | |
| 858, 2972, 4259, D939, D3288, D4752, D4754 | Host *S. thermophilus* DGCC7710 |
| D4090, D4807, D5821 | Host *S. thermophilus* DGCC7796 |
| *S. mutans* cos-type phage | |
| M102AD | Host *S. mutans* HER 1503 |

[1]SMQ-301 and phage DT1 are available at Félix d'Hérelle Reference Centre for Bacterial Viruses, under reference HER 1368 and HER 368 respectively DNA Isolation, Sequencing and Bioinformatics Analysis The genomic DNA of the BIMs was extracted as previously described (Bissonnette et al., 2000). The genomes were sequenced using the Illumina MiSeq platform. The libraries were prepared with the NEXTERA® XT DNA sample preparation kit according to the manufacturer's instructions and sequenced using MiSeq regents (2×250 nt paired-end). The average coverage ranged from 6.8- to 80.1-fold. The reads obtained for the genome of nine BIMs were aligned on the *S. thermophilus* SMQ-301 genome (Labrie et al., 2015) using Novoalign (www.novocraft.com) with the default setting. The mutations were extracted from the alignment file using SAMTools (Li et al., 2009). In-house Python scripts were used to map the mutation in the bacterial genome and translated into protein sequences. The mutations with the highest score as provided by SAMTools were considered first.

Complementation Assays

The *S. thermophilus* SMQ-301:MetAP$^{H206Q}$ strain was complemented with the metAP allele as set forth in SEQ ID NO:1 (metAP allele of SMQ-301). First, the metAP allele as set forth in SEQ ID NO:1 was cloned into pNZ123 using Gibson assembly. The vector pNZ123 was linearized with XbaI (Roche) according to the manufacturer's instructions. The insert was amplified with the primers SJL154 and SJL155 with Q5 high-fidelity DNA polymerase (NEB). Both primers had 30 nt extensions complementing the 3' and 5' ends, respectively, of the linearized vector. An insert/vector ratio of 3:1 was used for assembly. The master mixture for Gibson assembly was prepared as described previously (Gibson et al., 2009). The resulting construction was transformed into *E. coli* NEB5α according to the manufacturer's instructions and the clones were selected on LB media supplemented with 1% agar and 25 µg/mL chloramphenicol. One clone was confirmed by Sanger sequencing (ABI 3730xl) at the Plateforme de Séquençage et de Génotypage des Génomes at the CHUL Center. The plasmid DNA was extracted using a QlAprep Spin Miniprep kit (Qiagen) and transformed into *S. thermophilus* (Hynes et al., 2017). The clones were selected by spreading the transformation mixture on LM17 supplemented with 1% agar and 5 µg/mL of chloramphenicol.

Directed and Random Mutagenesis

The metAP allele with the desired mutation was amplified by PCR using the primers SJL128 and SJL130 (Table 2). At least 10 PCR reactions of 50 µL were done for each assay to obtain enough DNA for natural transformation. All reactions were pooled and precipitated by adding 1.5 mL of 95% ethanol and 75 µL of sodium acetate 3 M (pH 5.2). The tubes were centrifuged at 25,000×g for 20 min at 4° C. The DNA pellet was washed twice with 1 mL of 70% ethanol and let dry for 10 min at room temperature to remove traces of ethanol. Finally, the pellets were dissolved in 150 µL of water. The linear DNA fragments were introduced into *S. thermophilus* by natural transformation (Gardan et al., 2009). Briefly, *S. thermophilus* was grown overnight at 37° C. in 1 mL of LM17. The culture was centrifuged at 17,000×g for 1 min, the bacterial cells were washed twice with chemically defined media (CDM) and they were recovered in 1 mL of CDM. The final culture was diluted 30-fold to obtain an $OD_{600nm}$ of 0.05 and incubated 75 min at 37° C. before storing at −20° C. For the transformation, 1 µM of the peptide ComS and 1 µg of linear DNA were added to 300 µL of naturally competent cells. The mixture was incubated for 3 h at 37° C. The cells were serially diluted and spread on non-selective LM17 agar to obtain isolated colonies. The colonies were screened using a PCR approach specifically designed to detect clones with the desired mutation. One of the primers used in this protocol included the desired mutation at its 3' end. Thus, the PCR amplification was only positive if the mutation was present in the clone screened. The sequence of the primers SJL154 and SJL155 used for screening the transformants are listed in Table 2. For random mutagenesis, the same protocol as directed mutagenesis was used with the only exception that we added $MnSO_4$ (10 µM final) and phage DT1 was used for the selection of resistant clones.

TABLE 2

List of primers (*: described in Hynes et al. 2017)

| Primer | Sequence 5'-3' | Function |
|---|---|---|
| SJL128 | TCAATCTACTCAAGGTATGAATCA | Natural transformation |
| SJL130 | GTCAGTAGTAGTGGTCAAGA | of metAP |
| SJL150 | AGTTCCTGATAGGTCGCATT | Detection of the |
| SJL151 | GAGTTGGACCAACAATGCAG | mutation in metAP |
| SJL154 | CAGCAGCGGCCTGGTGCCGCGCGGCAGCCAAATGAT TACACTGAAATCAGCACGTG | Cloning metAP in pNZ123 |
| SJL155 | GCCGGATCTCAGTGGTGGTGGTGGTGGTGCTTAATAA GTTCTTTCTTCCCCTTGAG | |
| SJL160 | ATTACAGCTCCAGATCCAGTACTGAATTCTTGAGCCTG CTATGATTGACTCTGCA | Cloning mutated *S. mutans* metAP in |
| SJL161 | ATTGGGTTCTTCCTGCATGGTTGG | pNZ123 |
| SJL162 | CCAACCATGCAGGAAGAACCCAAT | |
| SJL163 | GAAAATATGCACTCGAGAAGCTTGAGCTCTCCGAAGG TGGACAACATAATAGC | |
| CM_145 | GAATTCGAATTCAAAGGCTGTTGTGACAGCAA | Cloning *S. mutans* |
| CM_146 | CTCGAGCTCGAGTTAATAAGTCCCTTCTTGACCC | metAP in pNZ123 |
| CR1-fwd* | TGCTGAGACAACCTAGTCTCTC | CR1 locus screening |
| CR1-revLong* | TAAACAGAGCCTCCCTATCC | |
| CR3-fwd* | CTGAGATTAATAGTGCGATTACG | CR3 locus screening |
| CR3-rev* | GCTGGATATTCGTATAACATGTC | |

Directed metAP mutagenesis in *Streptococcus mutans*

The allele of the metAP gene was amplified from *S. mutans* HER 1503 with two sets of primers containing the desired mutation (MetAP$^{H206Q}$). The two sets of primers (SJL160 and SJL161 as well as SJL162 and SJL163) generated two overlapping amplicons, with the mutation in the overlapping region. The two fragments were purified using the QIAquick PCR purification kit (Qiagen) and fused by Gibson Assembly (Gibson et al., 2009). A PCR was then performed on the Gibson Assembly sample using primers SJL160 and SJL163 to amplify the fused fragments. After purification using the QIAquick PCR purification kit, the mutated metAP amplicon was transformed into *S. mutans* HER 1503 by natural transformation; the competence Stimulating Peptide (CSP) ordered from Biomatik was added to 500 µl of an exponentially growing culture of *S. mutans* (OD$_{600nm}$ of 0.1) at a concentration of 1 µM along with 1 µg of purified mutated metAP amplicon (Dufour et al., 2011). The culture was incubated overnight at 37° C. with 5% CO$_2$, then mixed with the virulent phage M102AD in BHI supplemented with 0.7% agar and plated onto BHI supplemented with 1% agar. The metAP allele in the surviving derivative was amplified by PCR using primers SJL160 and SJL163 and sequenced to confirm the presence of the mutation.

For the complementation of the BIM *S. mutans* HER 1503:MetAP$^{H206Q}$, the metAP allele of the HER 1503*S. mutans* was cloned into pNZ123. pNZ123 was linearized with XhoI and EcoRI to remove the 24 base pairs between the two sites and the resulting plasmid was purified using the QIAquick Gel Extraction kit (Qiagen). The metAP allele was amplified from *S. mutans* HER 1503 using primers CM_145 and CM_146 to generate the gene, flanked by XhoI and EcoRI restriction sites. The PCR sample was purified using the QIAgen PCR purification kit, cut by XhoI and EcoRI and ligated into the linearized pNZ123 using T4 DNA ligase. The molar insert/vector ratio used during the ligation was 3:1. The ligated plasmid was transformed into *E. coli* NEB5α according to the manufacturer's instructions and plated onto solid LB media supplemented with 25 µg/mL chloramphenicol. Amplification of the metAP allele by primers CM_145 and CM_146 and sequencing confirmed the sequence cloned in the complementation plasmid. The plasmid DNA was extracted using a QIAprep Spin Miniprep kit and transformed in the *S. mutans* HER 1503: MetAP$^{H206Q}$. The strain was grown in BHI until an OD$_{600\ nm}$ of 0.1 was reached, an aliquot of 500 µL was exposed to 1 µM CSP and transformed with 1 µg of the complementation plasmid. After 2.5 hours incubation period at 37° C. with 5% CO$_2$, the culture was plates onto BHI+1% agar supplemented with 10 µg/mL of chloramphenicol.

Mutation Stability Test

To test the stability of the mutation H206Q, we inoculated (1%) the strains *S. thermophilus* SMQ-301 and DGCC7796 and their respective mutants [SMQ-301:MetAP$^{H206Q}$ and DGCC7796:MetAP$^{H206Q}$] in 10 mL of M17 medium (Nutri-Bact) and in reconstituted milk (10% nonfat dry milk). The strains were incubated at 42° C. during the day. Then, an inoculum of 1% was transferred to fresh media or milk and incubated at 37° C. for the night. After 9 transfers (5 days, 4 nights) corresponding to approximately 60 generations, we randomly selected 10 colonies from each of the four strains and tested them for sensitivity to phage DT1 (cos) for *S. thermophilus* SMQ-301 and *S. thermophilus* SMQ-301: MetAP$^{H206Q}$, and phages D4090 (cos) and D4274 (pac) for *S. thermophilus* DGCC7796 and *S. thermophilus* DGCC7796:MetAP$^{H206Q}$. Sequencing of the metAP gene and CR1 was done for SMQ-301 and SMQ-301: MetAP$^{H206Q}$ colonies with primers SJL128/SJL130 and CR1-fwd/CR1-rev to confirm the presence of the mutation after the transfers and the identity of the strain.

Example 1

A Mutation in the Gene Coding for the Methionine Aminopeptidase Reduces the Sensitivity to Phages Several BIMs of *S. thermophilus* SMQ-301 that had a reduced sensitivity to phage DT1 were isolated according to the protocol described above in the section entitled "Bacteriophage-insensitive mutant isolation". More than 95% of the BIMs had acquired new spacers targeting the phage DT1 genome in their CRISPR loci. Nine SMQ-301 BIMs were selected that had not acquired new spacers, conjecturing that they had a mutation elsewhere in the bacterial genome to provide a reduced sensitivity to phage DT1. The genomes of these nine non-CRISPR BIMs were sequenced. By comparing these sequences with the genome of the *S. thermophilus* SMQ-301 (Labrie et al., 2015) several mutations were found. Although many of these mutations may potentially be involved in phage infection, the same mutation (T→G) occurred at position 618 of the metAP gene of three of the nine BIMs. This gene codes for the methionine aminopeptidase (MetAP) and the mutation induces an amino acid substitution from a histidine to a glutamine at position 206 in the MetAP protein (H206Q). BLAST searches indicated that this histidine is conserved in all MetAP protein sequences analyzed. While the MetAP protein of *S. thermophilus* has not been previously studied, it shares 89% identity and 96% similarity with the MetAP protein of *Streptococcus pneumonia* TIGR4, which has been characterized, including at the structural level (PDB 4KM3) (Arya et al. 2013).

Example 2

A Mutation in the metAP Gene Reduces the Sensitivity to Phage in *S. thermophilus*

To confirm that the reduction of sensitivity to phage was due to the MetAP$^{H206Q}$ mutation—and not to other mutations in the genome—the allele coding for the MetAP$^{H206Q}$ protein was amplified and transformed into *S. thermophilus* SMQ-301 using natural competence. Although selecting with phages is very efficient, it drastically increases the odds of selecting CRISPR BIMs as well as for other mutations that confer reduced sensitivity to phage. Instead, a PCR strategy to detect the transformants that integrated the PCR product with the mutation into their genome, in the absence of phage selection, was designed. The primers SJL150 in combination with SJL151 with the desired mutation at its 3' end were used to specifically detect the mutation in the bacterial genome. To avoid false positives due to the potential presence of residual linear DNA from the transformation inside the bacterial cytoplasm, a primer that matched the flanking genomic region of the transformed DNA fragment was designed. A total of 282 clones were screened for integration of the H206Q metAP allele and four positive clones with the desired MetAP$^{H206Q}$ mutation were obtained. One of these clones, *S. thermophilus* SMQ-301: MetAP$^{H206Q}$, was randomly selected and its phage sensitivity determined by EOP assay I. No plaquing was visible on a bacterial culture with various dilutions of the phage lysate, indicating a very high phage resistance phenotype (EOP 10$^{-8}$, Table 3). Using various experimental conditions, attempts were made to isolate phage mutants that would overcome the effect of the H$^{206Q}$ MetAP, but to no avail. The incubation temperature was varied, anaerobic conditions used, different concentrations of glycine added to the media to weaken the bacterial cell wall, agar was replaced with different concentrations of agarose and rescue experiments in liquid media were attempted but still no phage DT1-derivatives able to propagate on the BIM SMQ-301:MetAP$^{H206Q}$ were obtained.

TABLE 3

Effect of S. thermophilus metAP mutations on phage efficiency of plaquing

| | Strain + pNZ123 (EOP) |
|---|---|
| S. thermophilus SMQ-301 | 1 |
| S. thermophilus SMQ-301 BIM #2 | $1.7 \times 10^{-8}$ |
| S. thermophilus SMQ-301 BIM #3 | $1.7 \times 10^{-8}$ |
| S. thermophilus SMQ-301 BIM #5 | $1.7 \times 10^{-8}$ |
| S. thermophilus SMQ-301:MetAP$^{H206Q}$ | $1.7 \times 10^{-8}$ |

Example 3

Complementation with the Allele of the metAP Gene of SMQ-301 Restores Phage Sensitivity The allele of the metAP gene of SMQ-301 was cloned into the shuttle expression vector pNZ123. The resulting construction was transformed into S. thermophilus SMQ-301:MetAP$^{H206Q}$ to complement the mutation in trans. Sensitivity to phage DT1 was restored for two out of three BIMs complemented with plasmid pNZ123:MetAP (Table 4), confirming that the MetAP$^{H206Q}$ substitution was responsible for the phage phenotype. Of note, for one BIM (#3), sensitivity to phage DT1 was not completely restored (EOP=0.02), suggesting that mutations in other gene(s) are likely involved in phage DT1 resistance (Table 4). The mutated metAP gene was also cloned into pNZ123 and transformed into S. thermophilus SMQ-301. There was no difference in EOP between the strain with pNZ123 when compared to the strain with pNZ123:MetAP$^{H206Q}$, suggesting that the mutation does not produce a dominant phenotype.

TABLE 4

Effect of complementation of S. thermophilus MetAP mutations on phage efficiency of plaquing

| | Strain + pNZ123:metAP (EOP) |
|---|---|
| S. thermophilus SMQ-301 | 1 |
| S. thermophilus SMQ-301 BIM #2 | 1.7 |
| S. thermophilus SMQ-301 BIM #3 | 0.02 |
| S. thermophilus SMQ-301 BIM #5 | 2.4 |
| S. thermophilus SMQ-301:MetAP$^{H206Q}$ | 1 |

Example 4

The MetAP H206Q Substitution has a Broad Range Against Cos-Type Phages

To determine if the resistance provided by the MetAP$^{H206Q}$ substitution is phage-dependent, the cos-type phage MD2, which is also capable of infecting SMQ-301, was tested. Phage MD2 was also severely inhibited by the H206Q MetAP.

To show that this mutation is not strain-dependent, MetAP$^{H206Q}$ was introduced into several S. thermophilus strains using directed mutagenesis. The mutation was introduced into the strain S. thermophilus DGCC782, which is sensitive to the cos-type phages N1032, N1117, N1119, N1169, N1358 and N3782. The mutation was also introduced into the strain S. thermophilus DGCC7710, which is sensitive to cos-type phages namely D5691, D5913, D6037 and D6215 and several pac-type phages, namely 858, 2972, D3288, 4259, D4752, D4754 and D939. Finally, the mutation was introduced into S. thermophilus DGCC7796, which is sensitive to several cos-type phages namely D4090, D5821, D4807 and D6179 and several pac-type namely D2765, D4274, D5787 and D5876. Although the mutation was less efficient against cos-type phages infecting S. thermophilus DGCC7710 (EOP $10^{-5}$), the mutation provided resistance against all cos-type phages tested. The introduction of the MetAP$^{H206Q}$ allele into S. thermophilus DGCC7796 and DGCC782 led to a reduction in the EOP of at least $10^{-6}$, which corresponded to the limit of detection (lysis zone with the dilution $10^{-1}$). Moreover, no phage mutant could be recovered from these assays. On the other hand, none of the S. thermophilus pac-type phages tested were affected by the mutation suggesting that MetAP is not important for the replication of the phages of this group.

To determine if the MetAP mutation would reduce the sensitivity to another bacterial species, the allele coding for the MetAP$^{H206Q}$ protein was introduced into the S. mutans strain HER 1503, which is sensitive to the cos-type phage M102AD (Delisle et al., 2012). The metAP gene of S. mutans HER 1503 has the same length (861 bp) as the gene of S. thermophilus SMQ-301. The two metAP genes share 74% identity while the two methionine aminopeptidases (MetAP protein) share 85% identity. The histidine residue found at position 206 is present in S. mutans. The insertion of the allele coding for the MetAP$^{H206Q}$ protein into the S. mutans genome (in lieu of the original metAP allele) provided a reduced sensitivity to phage M102AD (EOP<1× $10^{-7}$, Table 5). Complementation of the mutated strain with the original metAP allele restored the phage sensitivity phenotype (Table 5). Taken altogether, these data suggest a relatively widespread role of MetAP in phage replication.

TABLE 5

Effect of S. mutans MetAP mutations on phage efficiency of plaquing

| | Strain + pNZ123 (EOP) | Strain + pNZ123:MetAPSmut (EOP) |
|---|---|---|
| S. mutans HER 1503 | 1 | ND |
| S. mutans HER 1503:MetAP$^{H206Q}$ | $<1 \times 10^{-7}$ | 1.1 |

(ND = Not determined)

Example 5

Other Mutations in MetAP Reduce the Sensitivity to Phage DT1

To determine if other mutations in the metAP gene can reduce the sensitivity to phage DT1, an error-prone PCR amplification approach was used. The resulting PCR products were transformed into S. thermophilus SMQ-301 using natural competence. Since an antibiotic resistance marker was not introduced, phage DT1 was used to select the clones. The transformation assay with the positive control (MetAP$^{H206Q}$) resulted in many more BIMs than with the negative control (no DNA). The gene coding for the MetAP protein was sequenced and seven mutants had a mutation in the metAP gene resulting in the substitution of an amino acid. For 6 of these mutants, the original amino acid was replaced by another amino acid (Q57K, L153P, A168E, V228D, P233Q and P233L). For another mutant, the original amino acid was replaced by a stop codon (G226*) (Table 6).

The sensitivity to phage DT1 for these 7 mutants was retested and they all had a reduced sensitivity to phage DT1, with an EOP less than $1\times10^{-6}$. The resistant strains were complemented with pNZ123:MetAP and as previously observed, the MetAP as set forth in SEQ ID NO:2 restored the phage sensitivity phenotype, confirming that any of these 7 mutations in the MetAP protein reduces the sensitivity to cos-type phages.

TABLE 6

Random mutagenesis of the metAP gene of *S. thermophilus*

| BIM | Mutation | Codon change | Amino acid change | EOP | EOP after complementation |
|---|---|---|---|---|---|
| MetAP_S7 | C169A | CAG > AAG | Q57K | $<1.10^{-6}$ | $5.10^{-1}$ |
| MetAP_S45 | T458C | CTT > CCT | L153P | $<1.10^{-6}$ | $1.10^{0}$ |
| MetAP_S11 | C503A | GCG > GAG | A168E | $<1.10^{-6}$ | $3.10^{-3}$ |
| MetAP_R22 | T683A | GTC > GAC | V228D | $<1.10^{-6}$ | $1.10^{-1}$ |
| MetAP_S21 | G676T | GGA > TGA | G226* | $<1.10^{-6}$ | $3.10^{-1}$ |
| MetAP_S32 | C698A | CCA > CAA | P233Q | $<1.10^{-6}$ | $7.10^{-1}$ |
| MetAP_S36 | C698T | CCA > CTA | P233L | $<1.10^{-6}$ | $6.10^{-2}$ |

(*represents a stop codon)

Example 6

The MetAP$^{H206Q}$ Mutation is Stable.

One of the important features for industrial fermentation is the stability of the phage resistance phenotype. Thus, we verified the stability of the mutation MetAP$^{H206Q}$ over 60 generation of *S. thermophilus* SMQ-301 and DGCC7796 as well as their mutants in milk and LM17. While all selected colonies of the wild type strains remained phage sensitive, all 10 colonies from each mutant remained phage resistant indicating that the mutation MetAP$^{H206Q}$ is stable.

CONCLUSION

Here, it is demonstrated that a reduced sensitivity to cos-type phages can be acquired through mutations in the metAP gene of *S. thermophilus* and *S. mutans*. However, none of the mutations identified in the metAP gene reduces the sensitivity to pac-type phages. Finally, the inability to isolate phage mutants that overcame the MetAP H206Q substitution confirms that such mutation can provide a robust resistance phenotype.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A strain of the *Streptococcus* genus selected from the group consisting of a *Streptococcus thermophilus* strain and a *Streptococcus mutans* strain,
wherein the strain comprises a metAP$^R$ allele as the sole allele of its metAP gene, wherein the metAP$^R$ allele encodes a methionine aminopeptidase (MetAP$^R$) protein,
wherein the amino acid sequence of the MetAP$^R$ protein shares at least 80% sequence identity with the amino acid sequence set forth by SEQ ID NO: 2, and:
a) the MetAP$^R$ protein comprises an amino acid substitution at one or more positions corresponding to positions 57, 153, 168, 206, 228, or 233 of SEQ ID NO: 2; or
b) the MetAP$^R$ protein is C-terminally truncated at the position corresponding to position 226 of SEQ ID NO: 2.

2. The strain according to claim 1, wherein the substitution at one or more positions corresponding to positions 57, 153, 168, 206, 228, or 233 of SEQ ID NO: 2 is selected from the group consisting of a lysine at position 57, a proline at position 153, a glutamic acid at position 168, a glutamine at position 206, an aspartic acid at position 228, a glutamine at position 233 and a leucine at position 233.

3. A bacterial composition comprising the strain according to claim 1, and one or more lactic acid bacteria selected from the group consisting of *Streptococcus, Lactococcus, Lactobacillus, Leuconostoc, Pediococcus, Enterococcus, Oenococcus* and *Bifidobacterium*.

4. A food or feed product comprising the strain according to claim 1.

5. The strain according to claim 1, wherein the MetAP$^R$ protein is C-terminally truncated at the position corresponding to position 226 of SEQ ID NO: 2.

6. The strain according to claim 1, wherein the amino acid sequence of the MetAP$^R$ protein shares at least 90% sequence identity with the sequence set forth by SEQ ID NO: 2.

7. The strain according to claim 1, wherein the amino acid sequence of the MetAP$^R$ protein shares at least 95% sequence identity with the sequence set forth by SEQ ID NO: 2.

8. A food or feed product comprising the bacterial composition of claim 3.

* * * * *

SEQUENCE LISTING

```
<160> NUMBER OF SEQ ID NOS: 37

<210> SEQ ID NO 1
<211> LENGTH: 861
<212> TYPE: DNA
<213> ORGANISM: Streptococcus thermophilus

<400> SEQUENCE: 1
atgattacac tgaaatcagc acgtgaaatt gaagcgatgg atagagcggg agattttctt      60
gcaagtatcc acattggcct acgtgatctc ttgaaaccag gagtggatat gtgggaagta     120
gaagagtatg ttcgtcgtcg ttgtaaagaa gaaaatgttc tgccacttca gattgggtt      180 gaaggaagca tcatggacta tccttatgcg acatgttgta gtcttaatga tgaagtagca     240
cacgcttttc cacgtcatta tattttgaaa gatggagacc tcttgaaagt tgatatggtc     300
ttgtcagaac ctattgataa gtcagtgctt gatgtatcaa aattggactt tgataatgtt     360
gcccaggtaa aaaatatac agaatcatat gctggtggtt tggctgactc atgttgggca     420
tatgcgattg gaacgccttc tgatgaggtt aaaaaccta tggaagtaac ccgtgaagcc      480
atgtatcttg gtattgaaca agcgttagtt ggtaatcgta tcggtgatat cggtgcagct     540
atccaagaat acgctgaaag tcgaggctat ggtgtcgtac gtgatttggt cggacacgga     600
gttggaccaa caatgcatga agaaccaatg gttcctaact atggcgtggc tggacgtggt     660
cttcgcctta agaaggaat ggtcttgacc atcgagccaa tgattaacac aggaacttgg     720
gaaatcgata cagaccttga aactggttgg gctcataaga cacttgacgg tggcctttca     780
```

```
tgccaatatg agcaccaatt tgtaattact aaagatggtc cagtaatttt gacttctcaa    840
ggggaagaaa gaacttatta a                                              861
```

<210> SEQ ID NO 2
<211> LENGTH: 286
<212> TYPE: PRT
<213> ORGANISM: Streptococcus thermophilus

<400> SEQUENCE: 2

```
Met Ile Thr Leu Lys Ser Ala Arg Glu Ile Glu Ala Met Asp Arg Ala
1               5                   10                  15

Gly Asp Phe Leu Ala Ser Ile His Ile Gly Leu Arg Asp Leu Leu Lys
            20                  25                  30

Pro Gly Val Asp Met Trp Glu Val Glu Tyr Val Arg Arg Arg Cys
        35                  40                  45

Lys Glu Glu Asn Val Leu Pro Leu Gln Ile Gly Val Glu Gly Ser Ile
    50                  55                  60

Met Asp Tyr Pro Tyr Ala Thr Cys Cys Ser Leu Asn Asp Glu Val Ala
65                  70                  75                  80

His Ala Phe Pro Arg His Tyr Ile Leu Lys Asp Gly Asp Leu Leu Lys
                85                  90                  95

Val Asp Met Val Leu Ser Glu Pro Ile Asp Lys Ser Val Leu Asp Val
            100                 105                 110

Ser Lys Leu Asp Phe Asp Asn Val Ala Gln Val Lys Lys Tyr Thr Glu
        115                 120                 125

Ser Tyr Ala Gly Gly Leu Ala Asp Ser Cys Trp Ala Tyr Ala Ile Gly
    130                 135                 140

Thr Pro Ser Asp Glu Val Lys Asn Leu Met Glu Val Thr Arg Glu Ala
145                 150                 155                 160

Met Tyr Leu Gly Ile Glu Gln Ala Leu Val Gly Asn Arg Ile Gly Asp
                165                 170                 175

Ile Gly Ala Ala Ile Gln Glu Tyr Ala Glu Ser Arg Gly Tyr Gly Val
            180                 185                 190

Val Arg Asp Leu Val Gly His Gly Val Gly Pro Thr Met His Glu Glu
        195                 200                 205

Pro Met Val Pro Asn Tyr Gly Val Ala Gly Arg Gly Leu Arg Leu Lys
    210                 215                 220

Glu Gly Met Val Leu Thr Ile Glu Pro Met Ile Asn Thr Gly Thr Trp
225                 230                 235                 240

Glu Ile Asp Thr Asp Leu Glu Thr Gly Trp Ala His Lys Thr Leu Asp
                245                 250                 255

Gly Gly Leu Ser Cys Gln Tyr Glu His Gln Phe Val Thr Lys Asp
            260                 265                 270

Gly Pro Val Ile Leu Thr Ser Gln Gly Glu Glu Arg Thr Tyr
        275                 280                 285
```

<210> SEQ ID NO 3
<211> LENGTH: 861
<212> TYPE: DNA
<213> ORGANISM: Streptococcus thermophilus

<400> SEQUENCE: 3

```
atgattacac tgaaatcagc acgtgaaatt gaagcgatgg atagagcggg agattttctt    60
gcaagtatcc acattggcct acgtgatctc ttgaaaccag gagtggatat gtgggaagta   120
```

```
gaagagtatg ttcgtcgtcg ttgtaaagaa gaaaatgttc tgccacttca gattgggggtt    180 gaaggaagca tcatggacta tccttatgcg acatgttgta gtcttaatga tgaagtagca    240 cacgctttc  cacgtcatta tattttgaaa gatggagacc tcttgaaagt tgatatggtc    300
ttgtcagaac ctattgataa gtcagtgctt gatgtatcaa aattggactt tgataatgtt    360
gcccaggtaa aaaatatac  agaatcatat gctggtggtt tggctgactc atgttgggca    420
tatgcgattg gaacgccttc tgatgaggtt aaaaacctta tggaagtaac ccgtgaagcc    480
atgtatcttg gtattgaaca agcgttagtt ggtaatcgta tcggtgatat cggtgcagct    540
atccaagaat acgctgaaag tcgaggctat ggtgtcgtac gtgatttggt cggacacgga    600
gttggaccaa caatgcagga agaaccaatg gttcctaact atggcgtggc tggacgtggt    660
cttcgcctta agaaggaat  ggtcttgacc atcgagccaa tgattaacac aggaacttgg    720
gaaatcgata cagaccttga aactggttgg gctcataaga cacttgacgg tggccttttca   780 tgccaatatg agcaccaatt tgtaattact aaagatggtc cagtaatttt gacttctcaa    840
ggggaagaaa gaacttatta a                                              861
```

<210> SEQ ID NO 4
<211> LENGTH: 286
<212> TYPE: PRT
<213> ORGANISM: Streptococcus thermophilus

<400> SEQUENCE: 4

```
Met Ile Thr Leu Lys Ser Ala Arg Glu Ile Glu Ala Met Asp Arg Ala
1               5                   10                  15

Gly Asp Phe Leu Ala Ser Ile His Ile Gly Leu Arg Asp Leu Leu Lys
            20                  25                  30

Pro Gly Val Asp Met Trp Glu Val Glu Tyr Val Arg Arg Arg Cys
        35                  40                  45

Lys Glu Glu Asn Val Leu Pro Leu Gln Ile Gly Val Glu Gly Ser Ile
    50                  55                  60

Met Asp Tyr Pro Tyr Ala Thr Cys Cys Ser Leu Asn Asp Glu Val Ala
65                  70                  75                  80

His Ala Phe Pro Arg His Tyr Ile Leu Lys Asp Gly Asp Leu Leu Lys
                85                  90                  95

Val Asp Met Val Leu Ser Glu Pro Ile Asp Lys Ser Val Leu Asp Val
            100                 105                 110

Ser Lys Leu Asp Phe Asp Asn Val Ala Gln Val Lys Lys Tyr Thr Glu
        115                 120                 125

Ser Tyr Ala Gly Gly Leu Ala Asp Ser Cys Trp Ala Tyr Ala Ile Gly
    130                 135                 140

Thr Pro Ser Asp Glu Val Lys Asn Leu Met Glu Val Thr Arg Glu Ala
145                 150                 155                 160

Met Tyr Leu Gly Ile Glu Gln Ala Leu Val Gly Asn Arg Ile Gly Asp
                165                 170                 175

Ile Gly Ala Ala Ile Gln Glu Tyr Ala Glu Ser Arg Gly Tyr Gly Val
            180                 185                 190

Val Arg Asp Leu Val Gly His Gly Val Gly Pro Thr Met Gln Glu Glu
        195                 200                 205

Pro Met Val Pro Asn Tyr Gly Val Ala Gly Arg Gly Leu Arg Leu Lys
    210                 215                 220

Glu Gly Met Val Leu Thr Ile Glu Pro Met Ile Asn Thr Gly Thr Trp
225                 230                 235                 240
```

```
Glu Ile Asp Thr Asp Leu Glu Thr Gly Trp Ala His Lys Thr Leu Asp
            245                 250                 255

Gly Gly Leu Ser Cys Gln Tyr Glu His Gln Phe Val Ile Thr Lys Asp
        260                 265                 270

Gly Pro Val Ile Leu Thr Ser Gln Gly Glu Glu Arg Thr Tyr
        275                 280                 285

<210> SEQ ID NO 5
<211> LENGTH: 286
<212> TYPE: PRT
<213> ORGANISM: Streptococcus thermophilus
<220> FEATURE:
<221> NAME/KEY: misc_feature
<222> LOCATION: (57)..(57)
<223> OTHER INFORMATION: Xaa can be any naturally occurring amino acid,
      but not Gln

<400> SEQUENCE: 5

Met Ile Thr Leu Lys Ser Ala Arg Glu Ile Glu Ala Met Asp Arg Ala
1               5                   10                  15

Gly Asp Phe Leu Ala Ser Ile His Ile Gly Leu Arg Asp Leu Leu Lys
            20                  25                  30

Pro Gly Val Asp Met Trp Glu Val Glu Tyr Val Arg Arg Arg Cys
        35                  40                  45

Lys Glu Glu Asn Val Leu Pro Leu Xaa Ile Gly Val Glu Gly Ser Ile
50                  55                  60

Met Asp Tyr Pro Tyr Ala Thr Cys Cys Ser Leu Asn Asp Glu Val Ala
65                  70                  75                  80

His Ala Phe Pro Arg His Tyr Ile Leu Lys Asp Gly Asp Leu Leu Lys
            85                  90                  95

Val Asp Met Val Leu Ser Glu Pro Ile Asp Lys Ser Val Leu Asp Val
            100                 105                 110

Ser Lys Leu Asp Phe Asp Asn Val Ala Gln Val Lys Lys Tyr Thr Glu
        115                 120                 125

Ser Tyr Ala Gly Gly Leu Ala Asp Ser Cys Trp Ala Tyr Ala Ile Gly
        130                 135                 140

Thr Pro Ser Asp Glu Val Lys Asn Leu Met Glu Val Thr Arg Glu Ala
145                 150                 155                 160

Met Tyr Leu Gly Ile Glu Gln Ala Leu Val Gly Asn Arg Ile Gly Asp
                165                 170                 175

Ile Gly Ala Ala Ile Gln Glu Tyr Ala Glu Ser Arg Gly Tyr Gly Val
            180                 185                 190

Val Arg Asp Leu Val Gly His Gly Val Gly Pro Thr Met His Glu Glu
        195                 200                 205

Pro Met Val Pro Asn Tyr Gly Val Ala Gly Arg Gly Leu Arg Leu Lys
        210                 215                 220

Glu Gly Met Val Leu Thr Ile Glu Pro Met Ile Asn Thr Gly Thr Trp
225                 230                 235                 240

Glu Ile Asp Thr Asp Leu Glu Thr Gly Trp Ala His Lys Thr Leu Asp
            245                 250                 255

Gly Gly Leu Ser Cys Gln Tyr Glu His Gln Phe Val Ile Thr Lys Asp
        260                 265                 270

Gly Pro Val Ile Leu Thr Ser Gln Gly Glu Glu Arg Thr Tyr
        275                 280                 285

<210> SEQ ID NO 6
<211> LENGTH: 286
```

```
<212> TYPE: PRT
<213> ORGANISM: Streptococcus thermophilus
<220> FEATURE:
<221> NAME/KEY: misc_feature
<222> LOCATION: (153)..(153)
<223> OTHER INFORMATION: Xaa can be any naturally occurring amino acid,
      but not Leu

<400> SEQUENCE: 6

Met Ile Thr Leu Lys Ser Ala Arg Glu Ile Glu Ala Met Asp Arg Ala
1               5                   10                  15

Gly Asp Phe Leu Ala Ser Ile His Ile Gly Leu Arg Asp Leu Leu Lys
            20                  25                  30

Pro Gly Val Asp Met Trp Glu Val Glu Glu Tyr Val Arg Arg Arg Cys
        35                  40                  45

Lys Glu Glu Asn Val Leu Pro Leu Gln Ile Gly Val Glu Gly Ser Ile
50                  55                  60

Met Asp Tyr Pro Tyr Ala Thr Cys Cys Ser Leu Asn Asp Glu Val Ala
65                  70                  75                  80

His Ala Phe Pro Arg His Tyr Ile Leu Lys Asp Gly Asp Leu Leu Lys
                85                  90                  95

Val Asp Met Val Leu Ser Glu Pro Ile Asp Lys Ser Val Leu Asp Val
            100                 105                 110

Ser Lys Leu Asp Phe Asp Asn Val Ala Gln Val Lys Lys Tyr Thr Glu
        115                 120                 125

Ser Tyr Ala Gly Gly Leu Ala Asp Ser Cys Trp Ala Tyr Ala Ile Gly
130                 135                 140

Thr Pro Ser Asp Glu Val Lys Asn Xaa Met Glu Val Thr Arg Glu Ala
145                 150                 155                 160

Met Tyr Leu Gly Ile Glu Gln Ala Leu Val Gly Asn Arg Ile Gly Asp
                165                 170                 175

Ile Gly Ala Ala Ile Gln Glu Tyr Ala Glu Ser Arg Gly Tyr Gly Val
            180                 185                 190

Val Arg Asp Leu Val Gly His Gly Val Gly Pro Thr Met His Glu Glu
        195                 200                 205

Pro Met Val Pro Asn Tyr Gly Val Ala Gly Arg Gly Leu Arg Leu Lys
210                 215                 220

Glu Gly Met Val Leu Thr Ile Glu Pro Met Ile Asn Thr Gly Thr Trp
225                 230                 235                 240

Glu Ile Asp Thr Asp Leu Glu Thr Gly Trp Ala His Lys Thr Leu Asp
                245                 250                 255

Gly Gly Leu Ser Cys Gln Tyr Glu His Gln Phe Val Ile Thr Lys Asp
            260                 265                 270

Gly Pro Val Ile Leu Thr Ser Gln Gly Glu Glu Arg Thr Tyr
        275                 280                 285

<210> SEQ ID NO 7
<211> LENGTH: 286
<212> TYPE: PRT
<213> ORGANISM: Streptococcus thermophilus
<220> FEATURE:
<221> NAME/KEY: misc_feature
<222> LOCATION: (168)..(168)
<223> OTHER INFORMATION: Xaa can be any naturally occurring amino acid,
      but not Ala

<400> SEQUENCE: 7

Met Ile Thr Leu Lys Ser Ala Arg Glu Ile Glu Ala Met Asp Arg Ala
1               5                   10                  15
```

Gly Asp Phe Leu Ala Ser Ile His Ile Gly Leu Arg Asp Leu Leu Lys
            20                  25                  30

Pro Gly Val Asp Met Trp Glu Val Glu Glu Tyr Val Arg Arg Arg Cys
        35                  40                  45

Lys Glu Glu Asn Val Leu Pro Leu Gln Ile Gly Val Glu Gly Ser Ile
 50                  55                  60

Met Asp Tyr Pro Tyr Ala Thr Cys Cys Ser Leu Asn Asp Glu Val Ala
 65                  70                  75                  80

His Ala Phe Pro Arg His Tyr Ile Leu Lys Asp Gly Asp Leu Leu Lys
                85                  90                  95

Val Asp Met Val Leu Ser Glu Pro Ile Asp Lys Ser Val Leu Asp Val
            100                 105                 110

Ser Lys Leu Asp Phe Asp Asn Val Ala Gln Val Lys Lys Tyr Thr Glu
            115                 120                 125

Ser Tyr Ala Gly Gly Leu Ala Asp Ser Cys Trp Ala Tyr Ala Ile Gly
130                 135                 140

Thr Pro Ser Asp Glu Val Lys Asn Leu Met Glu Val Thr Arg Glu Ala
145                 150                 155                 160

Met Tyr Leu Gly Ile Glu Gln Xaa Leu Val Gly Asn Arg Ile Gly Asp
                165                 170                 175

Ile Gly Ala Ala Ile Gln Glu Tyr Ala Glu Ser Arg Gly Tyr Gly Val
            180                 185                 190

Val Arg Asp Leu Val Gly His Gly Val Gly Pro Thr Met His Glu Glu
        195                 200                 205

Pro Met Val Pro Asn Tyr Gly Val Ala Gly Arg Gly Leu Arg Leu Lys
            210                 215                 220

Glu Gly Met Val Leu Thr Ile Glu Pro Met Ile Asn Thr Gly Thr Trp
225                 230                 235                 240

Glu Ile Asp Thr Asp Leu Glu Thr Gly Trp Ala His Lys Thr Leu Asp
                245                 250                 255

Gly Gly Leu Ser Cys Gln Tyr Glu His Gln Phe Val Ile Thr Lys Asp
            260                 265                 270

Gly Pro Val Ile Leu Thr Ser Gln Gly Glu Glu Arg Thr Tyr
            275                 280                 285

<210> SEQ ID NO 8
<211> LENGTH: 286
<212> TYPE: PRT
<213> ORGANISM: Streptococcus thermophilus
<220> FEATURE:
<221> NAME/KEY: misc_feature
<222> LOCATION: (206)..(206)
<223> OTHER INFORMATION: Xaa can be any naturally occurring amino acid,
      but not His

<400> SEQUENCE: 8

Met Ile Thr Leu Lys Ser Ala Arg Glu Ile Glu Ala Met Asp Arg Ala
1               5                   10                  15

Gly Asp Phe Leu Ala Ser Ile His Ile Gly Leu Arg Asp Leu Leu Lys
            20                  25                  30

Pro Gly Val Asp Met Trp Glu Val Glu Glu Tyr Val Arg Arg Arg Cys
        35                  40                  45

Lys Glu Glu Asn Val Leu Pro Leu Gln Ile Gly Val Glu Gly Ser Ile
 50                  55                  60

Met Asp Tyr Pro Tyr Ala Thr Cys Cys Ser Leu Asn Asp Glu Val Ala
65                  70                  75                  80

```
His Ala Phe Pro Arg His Tyr Ile Leu Lys Asp Gly Asp Leu Leu Lys
                85                  90                  95

Val Asp Met Val Leu Ser Glu Pro Ile Asp Lys Ser Val Leu Asp Val
            100                 105                 110

Ser Lys Leu Asp Phe Asp Asn Val Ala Gln Val Lys Lys Tyr Thr Glu
        115                 120                 125

Ser Tyr Ala Gly Gly Leu Ala Asp Ser Cys Trp Ala Tyr Ala Ile Gly
    130                 135                 140

Thr Pro Ser Asp Glu Val Lys Asn Leu Met Glu Val Thr Arg Glu Ala
145                 150                 155                 160

Met Tyr Leu Gly Ile Glu Gln Ala Leu Val Gly Asn Arg Ile Gly Asp
                165                 170                 175

Ile Gly Ala Ala Ile Gln Glu Tyr Ala Glu Ser Arg Gly Tyr Gly Val
            180                 185                 190

Val Arg Asp Leu Val Gly His Gly Val Gly Pro Thr Met Xaa Glu Glu
        195                 200                 205

Pro Met Val Pro Asn Tyr Gly Val Ala Gly Arg Gly Leu Arg Leu Lys
    210                 215                 220

Glu Gly Met Val Leu Thr Ile Glu Pro Met Ile Asn Thr Gly Thr Trp
225                 230                 235                 240

Glu Ile Asp Thr Asp Leu Glu Thr Gly Trp Ala His Lys Thr Leu Asp
                245                 250                 255

Gly Gly Leu Ser Cys Gln Tyr Glu His Gln Phe Val Ile Thr Lys Asp
            260                 265                 270

Gly Pro Val Ile Leu Thr Ser Gln Gly Glu Glu Arg Thr Tyr
        275                 280                 285

<210> SEQ ID NO 9
<211> LENGTH: 286
<212> TYPE: PRT
<213> ORGANISM: Streptococcus thermophilus
<220> FEATURE:
<221> NAME/KEY: misc_feature
<222> LOCATION: (228)..(228)
<223> OTHER INFORMATION: Xaa can be any naturally occurring amino acid,
      but not Val

<400> SEQUENCE: 9

Met Ile Thr Leu Lys Ser Ala Arg Glu Ile Glu Ala Met Asp Arg Ala
1               5                   10                  15

Gly Asp Phe Leu Ala Ser Ile His Ile Gly Leu Arg Asp Leu Leu Lys
            20                  25                  30

Pro Gly Val Asp Met Trp Glu Val Glu Glu Tyr Val Arg Arg Arg Cys
        35                  40                  45

Lys Glu Glu Asn Val Leu Pro Leu Gln Ile Gly Val Glu Gly Ser Ile
    50                  55                  60

Met Asp Tyr Pro Tyr Ala Thr Cys Cys Ser Leu Asn Asp Glu Val Ala
65                  70                  75                  80

His Ala Phe Pro Arg His Tyr Ile Leu Lys Asp Gly Asp Leu Leu Lys
                85                  90                  95

Val Asp Met Val Leu Ser Glu Pro Ile Asp Lys Ser Val Leu Asp Val
            100                 105                 110

Ser Lys Leu Asp Phe Asp Asn Val Ala Gln Val Lys Lys Tyr Thr Glu
        115                 120                 125

Ser Tyr Ala Gly Gly Leu Ala Asp Ser Cys Trp Ala Tyr Ala Ile Gly
    130                 135                 140
```

Thr Pro Ser Asp Glu Val Lys Asn Leu Met Glu Val Thr Arg Glu Ala
145                 150                 155                 160

Met Tyr Leu Gly Ile Glu Gln Ala Leu Val Gly Asn Arg Ile Gly Asp
            165                 170                 175

Ile Gly Ala Ala Ile Gln Glu Tyr Ala Glu Ser Arg Gly Tyr Gly Val
        180                 185                 190

Val Arg Asp Leu Val Gly His Gly Val Gly Pro Thr Met His Glu Glu
    195                 200                 205

Pro Met Val Pro Asn Tyr Gly Val Ala Gly Arg Gly Leu Arg Leu Lys
210                 215                 220

Glu Gly Met Xaa Leu Thr Ile Glu Pro Met Ile Asn Thr Gly Thr Trp
225                 230                 235                 240

Glu Ile Asp Thr Asp Leu Glu Thr Gly Trp Ala His Lys Thr Leu Asp
                245                 250                 255

Gly Gly Leu Ser Cys Gln Tyr Glu His Gln Phe Val Ile Thr Lys Asp
            260                 265                 270

Gly Pro Val Ile Leu Thr Ser Gln Gly Glu Glu Arg Thr Tyr
        275                 280                 285

<210> SEQ ID NO 10
<211> LENGTH: 286
<212> TYPE: PRT
<213> ORGANISM: Streptococcus thermophilus
<220> FEATURE:
<221> NAME/KEY: misc_feature
<222> LOCATION: (233)..(233)
<223> OTHER INFORMATION: Xaa can be any naturally occurring amino acid,
      but not Pro

<400> SEQUENCE: 10

Met Ile Thr Leu Lys Ser Ala Arg Glu Ile Glu Ala Met Asp Arg Ala
1               5                   10                  15

Gly Asp Phe Leu Ala Ser Ile His Ile Gly Leu Arg Asp Leu Leu Lys
            20                  25                  30

Pro Gly Val Asp Met Trp Glu Val Glu Glu Tyr Val Arg Arg Arg Cys
        35                  40                  45

Lys Glu Glu Asn Val Leu Pro Leu Gln Ile Gly Val Glu Gly Ser Ile
50                  55                  60

Met Asp Tyr Pro Tyr Ala Thr Cys Cys Ser Leu Asn Asp Glu Val Ala
65                  70                  75                  80

His Ala Phe Pro Arg His Tyr Ile Leu Lys Asp Gly Asp Leu Leu Lys
                85                  90                  95

Val Asp Met Val Leu Ser Glu Pro Ile Asp Lys Ser Val Leu Asp Val
            100                 105                 110

Ser Lys Leu Asp Phe Asp Asn Val Ala Gln Val Lys Lys Tyr Thr Glu
        115                 120                 125

Ser Tyr Ala Gly Gly Leu Ala Asp Ser Cys Trp Ala Tyr Ala Ile Gly
    130                 135                 140

Thr Pro Ser Asp Glu Val Lys Asn Leu Met Glu Val Thr Arg Glu Ala
145                 150                 155                 160

Met Tyr Leu Gly Ile Glu Gln Ala Leu Val Gly Asn Arg Ile Gly Asp
            165                 170                 175

Ile Gly Ala Ala Ile Gln Glu Tyr Ala Glu Ser Arg Gly Tyr Gly Val
        180                 185                 190

Val Arg Asp Leu Val Gly His Gly Val Gly Pro Thr Met His Glu Glu
    195                 200                 205

Pro Met Val Pro Asn Tyr Gly Val Ala Gly Arg Gly Leu Arg Leu Lys
    210                 215                 220

Glu Gly Met Val Leu Thr Ile Glu Xaa Met Ile Asn Thr Gly Thr Trp
225                 230                 235                 240

Glu Ile Asp Thr Asp Leu Glu Thr Gly Trp Ala His Lys Thr Leu Asp
                245                 250                 255

Gly Gly Leu Ser Cys Gln Tyr Glu His Gln Phe Val Ile Thr Lys Asp
            260                 265                 270

Gly Pro Val Ile Leu Thr Ser Gln Gly Glu Glu Arg Thr Tyr
        275                 280                 285

<210> SEQ ID NO 11
<211> LENGTH: 286
<212> TYPE: PRT
<213> ORGANISM: Streptococcus thermophilus

<400> SEQUENCE: 11

Met Ile Thr Leu Lys Ser Ala Arg Glu Ile Glu Ala Met Asp Arg Ala
1               5                   10                  15

Gly Asp Phe Leu Ala Ser Ile His Ile Gly Leu Arg Asp Leu Leu Lys
            20                  25                  30

Pro Gly Val Asp Met Trp Glu Val Glu Glu Tyr Val Arg Arg Arg Cys
        35                  40                  45

Lys Glu Glu Asn Val Leu Pro Leu Lys Ile Gly Val Glu Gly Ser Ile
    50                  55                  60

Met Asp Tyr Pro Tyr Ala Thr Cys Cys Ser Leu Asn Asp Glu Val Ala
65                  70                  75                  80

His Ala Phe Pro Arg His Tyr Ile Leu Lys Asp Gly Asp Leu Leu Lys
                85                  90                  95

Val Asp Met Val Leu Ser Glu Pro Ile Asp Lys Ser Val Leu Asp Val
            100                 105                 110

Ser Lys Leu Asp Phe Asp Asn Val Ala Gln Val Lys Lys Tyr Thr Glu
        115                 120                 125

Ser Tyr Ala Gly Gly Leu Ala Asp Ser Cys Trp Ala Tyr Ala Ile Gly
    130                 135                 140

Thr Pro Ser Asp Glu Val Lys Asn Leu Met Glu Val Thr Arg Glu Ala
145                 150                 155                 160

Met Tyr Leu Gly Ile Glu Gln Ala Leu Val Gly Asn Arg Ile Gly Asp
                165                 170                 175

Ile Gly Ala Ala Ile Gln Glu Tyr Ala Glu Ser Arg Gly Tyr Gly Val
            180                 185                 190

Val Arg Asp Leu Val Gly His Gly Val Gly Pro Thr Met His Glu Glu
        195                 200                 205

Pro Met Val Pro Asn Tyr Gly Val Ala Gly Arg Gly Leu Arg Leu Lys
    210                 215                 220

Glu Gly Met Val Leu Thr Ile Glu Pro Met Ile Asn Thr Gly Thr Trp
225                 230                 235                 240

Glu Ile Asp Thr Asp Leu Glu Thr Gly Trp Ala His Lys Thr Leu Asp
                245                 250                 255

Gly Gly Leu Ser Cys Gln Tyr Glu His Gln Phe Val Ile Thr Lys Asp
            260                 265                 270

Gly Pro Val Ile Leu Thr Ser Gln Gly Glu Glu Arg Thr Tyr
        275                 280                 285

```
<210> SEQ ID NO 12
<211> LENGTH: 286
<212> TYPE: PRT
<213> ORGANISM: Streptococcus thermophilus

<400> SEQUENCE: 12

Met Ile Thr Leu Lys Ser Ala Arg Glu Ile Glu Ala Met Asp Arg Ala
1               5                   10                  15

Gly Asp Phe Leu Ala Ser Ile His Ile Gly Leu Arg Asp Leu Leu Lys
            20                  25                  30

Pro Gly Val Asp Met Trp Glu Val Glu Tyr Val Arg Arg Arg Cys
        35                  40                  45

Lys Glu Glu Asn Val Leu Pro Leu Gln Ile Gly Val Glu Gly Ser Ile
50                  55                  60

Met Asp Tyr Pro Tyr Ala Thr Cys Cys Ser Leu Asn Asp Glu Val Ala
65                  70                  75                  80

His Ala Phe Pro Arg His Tyr Ile Leu Lys Asp Gly Asp Leu Leu Lys
                85                  90                  95

Val Asp Met Val Leu Ser Glu Pro Ile Asp Lys Ser Val Leu Asp Val
            100                 105                 110

Ser Lys Leu Asp Phe Asp Asn Val Ala Gln Val Lys Lys Tyr Thr Glu
        115                 120                 125

Ser Tyr Ala Gly Gly Leu Ala Asp Ser Cys Trp Ala Tyr Ala Ile Gly
    130                 135                 140

Thr Pro Ser Asp Glu Val Lys Asn Pro Met Glu Val Thr Arg Glu Ala
145                 150                 155                 160

Met Tyr Leu Gly Ile Glu Gln Ala Leu Gly Asn Arg Ile Gly Asp
                165                 170                 175

Ile Gly Ala Ala Ile Gln Glu Tyr Ala Glu Ser Arg Gly Tyr Gly Val
            180                 185                 190

Val Arg Asp Leu Val Gly His Gly Val Gly Pro Thr Met His Glu Glu
        195                 200                 205

Pro Met Val Pro Asn Tyr Gly Val Ala Gly Arg Gly Leu Arg Leu Lys
210                 215                 220

Glu Gly Met Val Leu Thr Ile Glu Pro Met Ile Asn Thr Gly Thr Trp
225                 230                 235                 240

Glu Ile Asp Thr Asp Leu Glu Thr Gly Trp Ala His Lys Thr Leu Asp
                245                 250                 255

Gly Gly Leu Ser Cys Gln Tyr Glu His Gln Phe Val Ile Thr Lys Asp
            260                 265                 270

Gly Pro Val Ile Leu Thr Ser Gln Gly Glu Glu Arg Thr Tyr
        275                 280                 285

<210> SEQ ID NO 13
<211> LENGTH: 286
<212> TYPE: PRT
<213> ORGANISM: Streptococcus thermophilus

<400> SEQUENCE: 13

Met Ile Thr Leu Lys Ser Ala Arg Glu Ile Glu Ala Met Asp Arg Ala
1               5                   10                  15

Gly Asp Phe Leu Ala Ser Ile His Ile Gly Leu Arg Asp Leu Leu Lys
            20                  25                  30

Pro Gly Val Asp Met Trp Glu Val Glu Tyr Val Arg Arg Arg Cys
        35                  40                  45

Lys Glu Glu Asn Val Leu Pro Leu Gln Ile Gly Val Glu Gly Ser Ile
```

```
            50                  55                  60
Met Asp Tyr Pro Tyr Ala Thr Cys Cys Ser Leu Asn Asp Glu Val Ala
 65                  70                  75                  80

His Ala Phe Pro Arg His Tyr Ile Leu Lys Asp Gly Asp Leu Leu Lys
                     85                  90                  95

Val Asp Met Val Leu Ser Glu Pro Ile Asp Lys Ser Val Leu Asp Val
                100                 105                 110

Ser Lys Leu Asp Phe Asp Asn Val Ala Gln Val Lys Lys Tyr Thr Glu
            115                 120                 125

Ser Tyr Ala Gly Gly Leu Ala Asp Ser Cys Trp Ala Tyr Ala Ile Gly
            130                 135                 140

Thr Pro Ser Asp Glu Val Lys Asn Leu Met Glu Val Thr Arg Glu Ala
145                 150                 155                 160

Met Tyr Leu Gly Ile Glu Gln Glu Leu Val Gly Asn Arg Ile Gly Asp
                    165                 170                 175

Ile Gly Ala Ala Ile Gln Glu Tyr Ala Glu Ser Arg Gly Tyr Gly Val
                180                 185                 190

Val Arg Asp Leu Val Gly His Gly Val Gly Pro Thr Met His Glu Glu
            195                 200                 205

Pro Met Val Pro Asn Tyr Gly Val Ala Gly Arg Gly Leu Arg Leu Lys
            210                 215                 220

Glu Gly Met Val Leu Thr Ile Glu Pro Met Ile Asn Thr Gly Thr Trp
225                 230                 235                 240

Glu Ile Asp Thr Asp Leu Glu Thr Gly Trp Ala His Lys Thr Leu Asp
                    245                 250                 255

Gly Gly Leu Ser Cys Gln Tyr Glu His Gln Phe Val Ile Thr Lys Asp
                260                 265                 270

Gly Pro Val Ile Leu Thr Ser Gln Gly Glu Glu Arg Thr Tyr
            275                 280                 285

<210> SEQ ID NO 14
<211> LENGTH: 286
<212> TYPE: PRT
<213> ORGANISM: Streptococcus thermophilus

<400> SEQUENCE: 14

Met Ile Thr Leu Lys Ser Ala Arg Glu Ile Glu Ala Met Asp Arg Ala
 1                   5                  10                  15

Gly Asp Phe Leu Ala Ser Ile His Ile Gly Leu Arg Asp Leu Leu Lys
                 20                  25                  30

Pro Gly Val Asp Met Trp Glu Val Glu Tyr Val Arg Arg Cys
             35                  40                  45

Lys Glu Glu Asn Val Leu Pro Leu Gln Ile Gly Val Glu Gly Ser Ile
 50                  55                  60

Met Asp Tyr Pro Tyr Ala Thr Cys Cys Ser Leu Asn Asp Glu Val Ala
 65                  70                  75                  80

His Ala Phe Pro Arg His Tyr Ile Leu Lys Asp Gly Asp Leu Leu Lys
                     85                  90                  95

Val Asp Met Val Leu Ser Glu Pro Ile Asp Lys Ser Val Leu Asp Val
                100                 105                 110

Ser Lys Leu Asp Phe Asp Asn Val Ala Gln Val Lys Lys Tyr Thr Glu
            115                 120                 125

Ser Tyr Ala Gly Gly Leu Ala Asp Ser Cys Trp Ala Tyr Ala Ile Gly
            130                 135                 140
```

```
Thr Pro Ser Asp Glu Val Lys Asn Leu Met Glu Val Thr Arg Glu Ala
145                 150                 155                 160

Met Tyr Leu Gly Ile Glu Gln Ala Leu Val Gly Asn Arg Ile Gly Asp
                165                 170                 175

Ile Gly Ala Ala Ile Gln Glu Tyr Ala Glu Ser Arg Gly Tyr Gly Val
            180                 185                 190

Val Arg Asp Leu Val Gly His Gly Val Gly Pro Thr Met His Glu Glu
        195                 200                 205

Pro Met Val Pro Asn Tyr Gly Val Ala Gly Arg Gly Leu Arg Leu Lys
    210                 215                 220

Glu Gly Met Asp Leu Thr Ile Glu Pro Met Ile Asn Thr Gly Thr Trp
225                 230                 235                 240

Glu Ile Asp Thr Asp Leu Glu Thr Gly Trp Ala His Lys Thr Leu Asp
                245                 250                 255

Gly Gly Leu Ser Cys Gln Tyr Glu His Gln Phe Val Ile Thr Lys Asp
                260                 265                 270

Gly Pro Val Ile Leu Thr Ser Gln Gly Glu Glu Arg Thr Tyr
            275                 280                 285

<210> SEQ ID NO 15
<211> LENGTH: 286
<212> TYPE: PRT
<213> ORGANISM: Streptococcus thermophilus

<400> SEQUENCE: 15

Met Ile Thr Leu Lys Ser Ala Arg Glu Ile Glu Ala Met Asp Arg Ala
1               5                   10                  15

Gly Asp Phe Leu Ala Ser Ile His Ile Gly Leu Arg Asp Leu Leu Lys
                20                  25                  30

Pro Gly Val Asp Met Trp Glu Val Glu Tyr Val Arg Arg Arg Cys
            35                  40                  45

Lys Glu Glu Asn Val Leu Pro Leu Gln Ile Gly Val Glu Gly Ser Ile
    50                  55                  60

Met Asp Tyr Pro Tyr Ala Thr Cys Cys Ser Leu Asn Asp Glu Val Ala
65                  70                  75                  80

His Ala Phe Pro Arg His Tyr Ile Leu Lys Asp Gly Asp Leu Leu Lys
                85                  90                  95

Val Asp Met Val Leu Ser Glu Pro Ile Asp Lys Ser Val Leu Asp Val
            100                 105                 110

Ser Lys Leu Asp Phe Asp Asn Val Ala Gln Val Lys Lys Tyr Thr Glu
        115                 120                 125

Ser Tyr Ala Gly Gly Leu Ala Asp Ser Cys Trp Ala Tyr Ala Ile Gly
    130                 135                 140

Thr Pro Ser Asp Glu Val Lys Asn Leu Met Glu Val Thr Arg Glu Ala
145                 150                 155                 160

Met Tyr Leu Gly Ile Glu Gln Ala Leu Val Gly Asn Arg Ile Gly Asp
                165                 170                 175

Ile Gly Ala Ala Ile Gln Glu Tyr Ala Glu Ser Arg Gly Tyr Gly Val
            180                 185                 190

Val Arg Asp Leu Val Gly His Gly Val Gly Pro Thr Met His Glu Glu
        195                 200                 205

Pro Met Val Pro Asn Tyr Gly Val Ala Gly Arg Gly Leu Arg Leu Lys
    210                 215                 220

Glu Gly Met Val Leu Thr Ile Glu Gln Met Ile Asn Thr Gly Thr Trp
225                 230                 235                 240
```

Glu Ile Asp Thr Asp Leu Glu Thr Gly Trp Ala His Lys Thr Leu Asp
            245                 250                 255

Gly Gly Leu Ser Cys Gln Tyr Glu His Gln Phe Val Ile Thr Lys Asp
            260                 265                 270

Gly Pro Val Ile Leu Thr Ser Gln Gly Glu Glu Arg Thr Tyr
            275                 280                 285

<210> SEQ ID NO 16
<211> LENGTH: 286
<212> TYPE: PRT
<213> ORGANISM: Streptococcus thermophilus

<400> SEQUENCE: 16

Met Ile Thr Leu Lys Ser Ala Arg Glu Ile Glu Ala Met Asp Arg Ala
1               5                   10                  15

Gly Asp Phe Leu Ala Ser Ile His Ile Gly Leu Arg Asp Leu Leu Lys
            20                  25                  30

Pro Gly Val Asp Met Trp Glu Val Glu Tyr Val Arg Arg Cys
            35                  40                  45

Lys Glu Glu Asn Val Leu Pro Leu Gln Ile Gly Val Glu Gly Ser Ile
50                  55                  60

Met Asp Tyr Pro Tyr Ala Thr Cys Cys Ser Leu Asn Asp Glu Val Ala
65                  70                  75                  80

His Ala Phe Pro Arg His Tyr Ile Leu Lys Asp Gly Asp Leu Leu Lys
            85                  90                  95

Val Asp Met Val Leu Ser Glu Pro Ile Asp Lys Ser Val Leu Asp Val
            100                 105                 110

Ser Lys Leu Asp Phe Asp Asn Val Ala Gln Val Lys Lys Tyr Thr Glu
            115                 120                 125

Ser Tyr Ala Gly Gly Leu Ala Asp Ser Cys Trp Ala Tyr Ala Ile Gly
            130                 135                 140

Thr Pro Ser Asp Glu Val Lys Asn Leu Met Glu Val Thr Arg Glu Ala
145                 150                 155                 160

Met Tyr Leu Gly Ile Glu Gln Ala Leu Val Gly Asn Arg Ile Gly Asp
            165                 170                 175

Ile Gly Ala Ala Ile Gln Glu Tyr Ala Glu Ser Arg Gly Tyr Gly Val
            180                 185                 190

Val Arg Asp Leu Val Gly His Gly Val Gly Pro Thr Met His Glu Glu
            195                 200                 205

Pro Met Val Pro Asn Tyr Gly Val Ala Gly Arg Gly Leu Arg Leu Lys
            210                 215                 220

Glu Gly Met Val Leu Thr Ile Glu Leu Met Ile Asn Thr Gly Thr Trp
225                 230                 235                 240

Glu Ile Asp Thr Asp Leu Glu Thr Gly Trp Ala His Lys Thr Leu Asp
            245                 250                 255

Gly Gly Leu Ser Cys Gln Tyr Glu His Gln Phe Val Ile Thr Lys Asp
            260                 265                 270

Gly Pro Val Ile Leu Thr Ser Gln Gly Glu Glu Arg Thr Tyr
            275                 280                 285

<210> SEQ ID NO 17
<211> LENGTH: 225
<212> TYPE: PRT
<213> ORGANISM: Streptococcus thermophilus

<400> SEQUENCE: 17

```
Met Ile Thr Leu Lys Ser Ala Arg Glu Ile Glu Ala Met Asp Arg Ala
1               5                  10                  15

Gly Asp Phe Leu Ala Ser Ile His Ile Gly Leu Arg Asp Leu Leu Lys
                20                  25                  30

Pro Gly Val Asp Met Trp Glu Val Glu Tyr Val Arg Arg Cys
            35                  40                  45

Lys Glu Glu Asn Val Leu Pro Leu Gln Ile Gly Val Glu Gly Ser Ile
    50                  55                  60

Met Asp Tyr Pro Tyr Ala Thr Cys Cys Ser Leu Asn Asp Glu Val Ala
65                  70                  75                  80

His Ala Phe Pro Arg His Tyr Ile Leu Lys Asp Gly Asp Leu Leu Lys
                85                  90                  95

Val Asp Met Val Leu Ser Glu Pro Ile Asp Lys Ser Val Leu Asp Val
            100                 105                 110

Ser Lys Leu Asp Phe Asp Asn Val Ala Gln Val Lys Lys Tyr Thr Glu
    115                 120                 125

Ser Tyr Ala Gly Gly Leu Ala Asp Ser Cys Trp Ala Tyr Ala Ile Gly
    130                 135                 140

Thr Pro Ser Asp Glu Val Lys Asn Leu Met Glu Val Thr Arg Glu Ala
145                 150                 155                 160

Met Tyr Leu Gly Ile Glu Gln Ala Leu Val Gly Asn Arg Ile Gly Asp
                165                 170                 175

Ile Gly Ala Ala Ile Gln Glu Tyr Ala Glu Ser Arg Gly Tyr Gly Val
            180                 185                 190

Val Arg Asp Leu Val Gly His Gly Val Gly Pro Thr Met His Glu Glu
    195                 200                 205

Pro Met Val Pro Asn Tyr Gly Val Ala Gly Arg Gly Leu Arg Leu Lys
    210                 215                 220

Glu
225

<210> SEQ ID NO 18
<211> LENGTH: 861
<212> TYPE: DNA
<213> ORGANISM: Streptococcus mutans

<400> SEQUENCE: 18
atgattacgt taaaatcaca gcgtgaaatt gaagcgatgg atgaggcagg tgattttctg      60
gctagcattc atatcggttt gcgtgatttg attaaacccg gacttgatat gtggaaaatt    120
gaagaatatg ttcgcagacg ttgtaaggaa gagaactatc ttcccttaca aattggtgtt    180
gatgggcagc ttatggatta ccctacgca acttgctgcg gactcaatga tgaagttgca     240
cacgcctttc cacgtcatta tatcttgaaa gatggcgatc ttcttaaagt tgatatggta    300
cttggcggtc ccattgctaa gaagaccta gatgtctcaa aattgaattt tgacaatgtg    360
gctcaagtca aaaatatac agatagtttt cgtggcggtg tggctgattc ctgctgggcc    420
tatgccgttg gcgatgtttc tcaagaagta aagaatctaa tggcagtgac taaagagtgt    480
ctctatcgtg gaattgaaaa ggcagtagtt ggcaatcgta ttggtgacat tggagcagct    540
attcaagaat atgctgaggc aacggttat ggtgtcgtcc gtgatttagt tggtcatggt     600
gttggcccaa ccatgcatga agaacccaat gtaccgcatt atggcagagc aggacgtggt    660
ctgcgtttga agagggtat ggtcttaact attgaaccca tgattaatac aggcacttgg    720
gaaattgata ctgatatgaa caccggctgg gcacacaaaa cgcttgatgg cggattatcc    780
```
tgtcagtatg agcatcaatt tgtcattaca aaagacggtc cccgtattct aacgagtcag    840
ggtcaagaag ggacttatta a                                              861

<210> SEQ ID NO 19
<211> LENGTH: 286
<212> TYPE: PRT
<213> ORGANISM: Streptococcus mutans

<400> SEQUENCE: 19

Met Ile Thr Leu Lys Ser Gln Arg Glu Ile Glu Ala Met Asp Glu Ala
1               5                   10                  15

Gly Asp Phe Leu Ala Ser Ile His Ile Gly Leu Arg Asp Leu Ile Lys
            20                  25                  30

Pro Gly Leu Asp Met Trp Lys Ile Glu Glu Tyr Val Arg Arg Arg Cys
        35                  40                  45

Lys Glu Glu Asn Tyr Leu Pro Leu Gln Ile Gly Val Asp Gly Gln Leu
    50                  55                  60

Met Asp Tyr Pro Tyr Ala Thr Cys Cys Gly Leu Asn Asp Glu Val Ala
65                  70                  75                  80

His Ala Phe Pro Arg His Tyr Ile Leu Lys Asp Gly Asp Leu Leu Lys
                85                  90                  95

Val Asp Met Val Leu Gly Gly Pro Ile Ala Lys Glu Asp Leu Asp Val
            100                 105                 110

Ser Lys Leu Asn Phe Asp Asn Val Ala Gln Val Lys Lys Tyr Thr Asp
        115                 120                 125

Ser Phe Arg Gly Gly Val Ala Asp Ser Cys Trp Ala Tyr Ala Val Gly
    130                 135                 140

Asp Val Ser Gln Glu Val Lys Asn Leu Met Ala Val Thr Lys Glu Cys
145                 150                 155                 160

Leu Tyr Arg Gly Ile Glu Lys Ala Val Val Gly Asn Arg Ile Gly Asp
                165                 170                 175

Ile Gly Ala Ala Ile Gln Glu Tyr Ala Glu Ala Asn Gly Tyr Gly Val
            180                 185                 190

Val Arg Asp Leu Val Gly His Gly Val Gly Pro Thr Met His Glu Glu
        195                 200                 205

Pro Asn Val Pro His Tyr Gly Arg Ala Gly Arg Gly Leu Arg Leu Lys
    210                 215                 220

Glu Gly Met Val Leu Thr Ile Glu Pro Met Ile Asn Thr Gly Thr Trp
225                 230                 235                 240

Glu Ile Asp Thr Asp Met Asn Thr Gly Trp Ala His Lys Thr Leu Asp
                245                 250                 255

Gly Gly Leu Ser Cys Gln Tyr Glu His Gln Phe Val Ile Thr Lys Asp
            260                 265                 270

Gly Pro Arg Ile Leu Thr Ser Gln Gly Gln Glu Gly Thr Tyr
        275                 280                 285

<210> SEQ ID NO 20
<211> LENGTH: 861
<212> TYPE: DNA
<213> ORGANISM: Streptococcus mutans

<400> SEQUENCE: 20
atgattacgt taaaatcaca gcgtgaaatt gaagcgatgg atgaggcagg tgattttctg    60
gctagcattc atatcggttt gcgtgatttg attaaacccg gacttgatat gtggaaaatt   120

```
gaagaatatg ttcgcagacg ttgtaaggaa gagaactatc ttcccttaca aattggtgtt    180
gatgggcagc ttatggatta ccoctacgca acttgctgcg gactcaatga tgaagttgca    240
cacgcctttc cacgtcatta tatcttgaaa gatggcgatc ttcttaaagt tgatatggta    300
cttggcggtc ccattgctaa agaagaccta gatgtctcaa aattgaattt tgacaatgtg    360
gctcaagtca aaaatatac agatagtttt cgtggcggtg tggctgattc ctgctgggcc    420
tatgccgttg gcgatgtttc tcaagaagta aagaatctaa tggcagtgac taaagagtgt    480
ctctatcgtg gaattgaaaa ggcagtagtt ggcaatcgta ttggtgacat tggagcagct    540
attcaagaat atgctgaggc caacggttat ggtgtcgtcc gtgatttagt tggtcatggt    600
gttggcccaa ccatgcagga agaacccaat gtaccgcatt atggcagagc aggacgtggt    660
ctgcgtttga agagggtat ggtcttaact attgaaccca tgattaatac aggcacttgg    720
gaaattgata ctgatatgaa caccggctgg gcacacaaaa cgcttgatgg cggattatcc    780
tgtcagtatg agcatcaatt tgtcattaca aaagacggtc cccgtattct aacgagtcag    840
ggtcaagaag ggacttatta a                                              861
```

<210> SEQ ID NO 21
<211> LENGTH: 286
<212> TYPE: PRT
<213> ORGANISM: Streptococcus mutans

<400> SEQUENCE: 21

```
Met Ile Thr Leu Lys Ser Gln Arg Glu Ile Glu Ala Met Asp Glu Ala
1               5                   10                  15

Gly Asp Phe Leu Ala Ser Ile His Ile Gly Leu Arg Asp Leu Ile Lys
            20                  25                  30

Pro Gly Leu Asp Met Trp Lys Ile Glu Glu Tyr Val Arg Arg Cys
        35                  40                  45

Lys Glu Glu Asn Tyr Leu Pro Leu Gln Ile Gly Val Asp Gly Gln Leu
    50                  55                  60

Met Asp Tyr Pro Tyr Ala Thr Cys Cys Gly Leu Asn Asp Glu Val Ala
65                  70                  75                  80

His Ala Phe Pro Arg His Tyr Ile Leu Lys Asp Gly Asp Leu Leu Lys
                85                  90                  95

Val Asp Met Val Leu Gly Gly Pro Ile Ala Lys Glu Asp Leu Asp Val
            100                 105                 110

Ser Lys Leu Asn Phe Asp Asn Val Ala Gln Val Lys Lys Tyr Thr Asp
        115                 120                 125

Ser Phe Arg Gly Gly Val Ala Asp Ser Cys Trp Ala Tyr Ala Val Gly
    130                 135                 140

Asp Val Ser Gln Glu Val Lys Asn Leu Met Ala Val Thr Lys Glu Cys
145                 150                 155                 160

Leu Tyr Arg Gly Ile Glu Lys Ala Val Val Gly Asn Arg Ile Gly Asp
                165                 170                 175

Ile Gly Ala Ala Ile Gln Glu Tyr Ala Glu Ala Asn Gly Tyr Gly Val
            180                 185                 190

Val Arg Asp Leu Val Gly His Gly Val Gly Pro Thr Met Gln Glu Glu
        195                 200                 205

Pro Asn Val Pro His Tyr Gly Arg Ala Gly Arg Gly Leu Arg Leu Lys
    210                 215                 220

Glu Gly Met Val Leu Thr Ile Glu Pro Met Ile Asn Thr Gly Thr Trp
225                 230                 235                 240
```

```
Glu Ile Asp Thr Asp Met Asn Thr Gly Trp Ala His Lys Thr Leu Asp
                245                 250                 255

Gly Gly Leu Ser Cys Gln Tyr Glu His Gln Phe Val Ile Thr Lys Asp
            260                 265                 270

Gly Pro Arg Ile Leu Thr Ser Gln Gly Gln Glu Gly Thr Tyr
        275                 280                 285

<210> SEQ ID NO 22
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 22
tcaatctact caaggtatga atca                                          24

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 23
gtcagtagta gtggtcaaga                                               20

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 24
agttcctgat aggtcgcatt                                               20

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 25
gagttggacc aacaatgcag                                               20

<210> SEQ ID NO 26
<211> LENGTH: 56
<212> TYPE: DNA
<213> ORGANISM: Artificial Sequence
<220> FEATURE:
<223> OTHER INFORMATION: Oligonucleotide primer

<400> SEQUENCE: 26
cagcagcggc ctggtgccgc gcggcagcca aatgattaca ctgaaatcag cacgtg       56

<210> SEQ ID NO 27
<211> LENGTH: 56
<212> TYPE: DNA
<213> ORGANISM: Artificial Sequence
<220> FEATURE:
<223> OTHER INFORMATION: Oligonucleotide primer

<400> SEQUENCE: 27
```
gccggatctc agtggtggtg gtggtggtgc ttaataagtt ctttcttccc cttgag         56

<210> SEQ ID NO 28
<211> LENGTH: 55
<212> TYPE: DNA
<213> ORGANISM: Artificial Sequence
<220> FEATURE:
<223> OTHER INFORMATION: Oligonucleotide primer

<400> SEQUENCE: 28
attacagctc cagatccagt actgaattct tgagcctgct atgattgact ctgca         55

<210> SEQ ID NO 29
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 29
attgggttct tcctgcatgg ttgg                                            24

<210> SEQ ID NO 30
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 30
ccaaccatgc aggaagaacc caat                                            24

<210> SEQ ID NO 31
<211> LENGTH: 53
<212> TYPE: DNA
<213> ORGANISM: Artificial Sequence
<220> FEATURE:
<223> OTHER INFORMATION: Oligonucleotide primer

<400> SEQUENCE: 31
gaaaatatgc actcgagaag cttgagctct ccgaaggtgg acaacataat agc            53

<210> SEQ ID NO 32
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 32
gaattcgaat tcaaaggctg ttgtgacagc aa                                   32

<210> SEQ ID NO 33
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 33
ctcgagctcg agttaataag tcccttcttg accc                                 34

<210> SEQ ID NO 34
<211> LENGTH: 22
<212> TYPE: DNA
<213> ORGANISM: Artificial Sequence

```
<220> FEATURE:
<223> OTHER INFORMATION: Oligonucleotide primer

<400> SEQUENCE: 34
tgctgagaca acctagtctc tc                                                22

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 35
taaacagagc ctccctatcc                                                   20

<210> SEQ ID NO 36
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 36
ctgagattaa tagtgcgatt acg                                               23

<210> SEQ ID NO 37
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 37
gctggatatt cgtataacat gtc                                               23
```